United States Patent
Mansfield et al.

(10) Patent No.: US 9,891,145 B1
(45) Date of Patent: Feb. 13, 2018

(54) COTTON SAMPLING SYSTEM

(71) Applicant: Quantitative Engineering Solutions, LLC, Farragut, TN (US)

(72) Inventors: Joe H. Mansfield, Alcoa, TN (US); Ken Campbell, Farragut, TN (US); Clark A. Roberts, Maryville, TN (US)

(73) Assignee: Quantitative Engineering Solutions, LLC, Farragut, TN (US)

( * ) Notice: Subject to any disclaimer, the term of this patent is extended or adjusted under 35 U.S.C. 154(b) by 63 days.

(21) Appl. No.: 14/690,299

(22) Filed: Apr. 17, 2015

Related U.S. Application Data

(63) Continuation-in-part of application No. 14/048,635, filed on Oct. 8, 2013, now Pat. No. 9,719,888.

(60) Provisional application No. 61/711,357, filed on Oct. 9, 2012, provisional application No. 61/981,421, filed on Apr. 18, 2014.

(51) Int. Cl.
  *G01N 1/28* (2006.01)
  *G01N 33/36* (2006.01)

(52) U.S. Cl.
  CPC .......... *G01N 1/28* (2013.01); *G01N 33/362* (2013.01)

(58) Field of Classification Search
  CPC ........ G01N 1/28; G01N 33/36; G01N 33/362; D01G 99/00; D01G 99/005
  See application file for complete search history.

(56) References Cited

U.S. PATENT DOCUMENTS

| | | | |
|---|---|---|---|
| 2,582,219 A | 1/1952 | Ardito et al. | |
| 4,903,374 A * | 2/1990 | Hosel | D01G 7/10 19/80 R |
| 5,367,747 A | 11/1994 | Shofner et al. | |
| 5,636,546 A * | 6/1997 | Frydrych | D01G 31/00 374/51 |
| 5,646,405 A * | 7/1997 | Nevel | D01B 3/025 250/330 |
| 5,819,373 A * | 10/1998 | Schlichter | B07C 5/342 19/0.21 |
| 5,892,142 A | 4/1999 | Ghorashi et al. | |
| 5,943,907 A * | 8/1999 | Ghorashi | G01N 33/362 19/66.1 |
| 6,085,584 A * | 7/2000 | Ramachandran | G01N 33/36 73/159 |

(Continued)

*Primary Examiner* — Natalie Huls
(74) *Attorney, Agent, or Firm* — Knox Patents; Thomas A. Kulaga

(57) ABSTRACT

Apparatus for a cotton sampling system. The system includes a first station that provides a stream of samples to a main conveyor. The main conveyor routes the samples to a testing station that includes a sub-sampler, an automated cotton containment mechanism, an indexer, and an HVI. The conveyors include a shroud that moves samples over and under the conveyor. In this way samples that need to be retested pass to the testing station after failing the first test. The sub-sampler includes a walking beam mechanism to advance the samples into a fiber extraction mechanism. The automated cotton containment mechanism includes a gate valve and a diverter valve. The gate valve has a normal position configured to allow passage of cotton fibers, but blocking clumps. Upon detection of a clump, the diverter valve operates and the gate valve opens so that the clump is diverted to a waste receptacle.

13 Claims, 19 Drawing Sheets

(56) References Cited

U.S. PATENT DOCUMENTS

| | | | | |
|---|---|---|---|---|
| 6,098,454 | A | * 8/2000 | Ghorashi | G01N 33/362 73/160 |
| 6,112,131 | A | * 8/2000 | Ghorashi | G01N 33/362 700/142 |
| 6,161,441 | A | 12/2000 | Ghorashi et al. | |
| 7,143,642 | B1 | * 12/2006 | Baxter | G01N 33/362 73/159 |
| 9,599,544 | B2 | * 3/2017 | Hart | G01N 1/286 |
| 2008/0267446 | A1 | * 10/2008 | Capewell | G01N 21/8483 382/100 |
| 2014/0096623 | A1 | * 4/2014 | Mansfield | G01N 1/04 73/863.21 |

\* cited by examiner

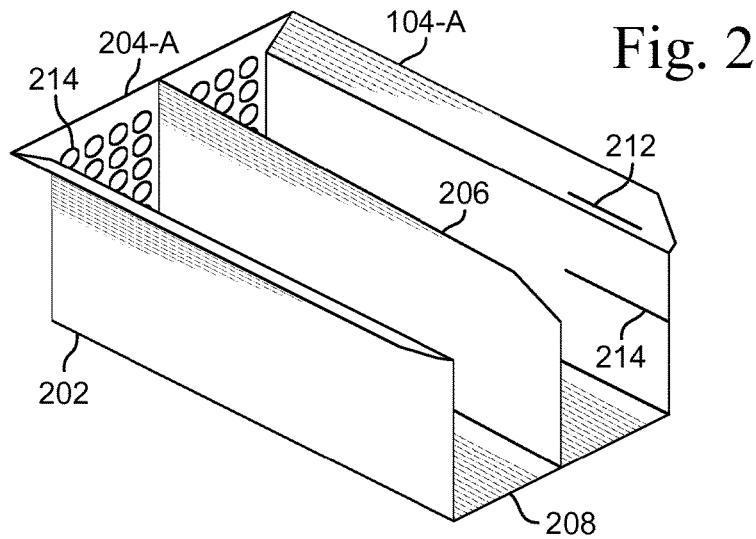
Fig. 2
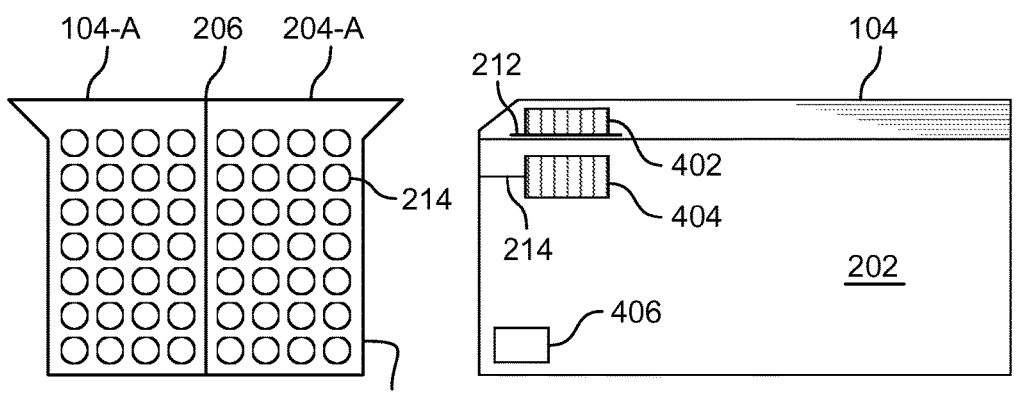
Fig. 3
Fig. 4
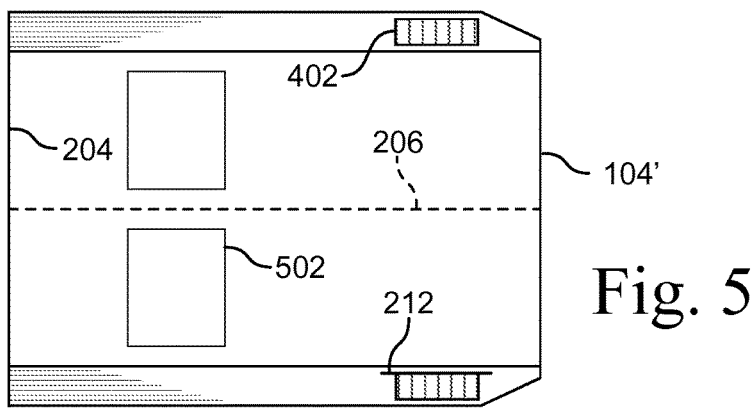
Fig. 5

COTTON SAMPLING SYSTEM

CROSS-REFERENCE TO RELATED APPLICATIONS

This application is a continuation-in-part of prior application Ser. No. 14/048,635, filed on Oct. 8, 2013, which claims the benefit of U.S. Provisional Application No. 61/711,357, filed Oct. 9, 2012, and this application claims the benefit of U.S. Provisional Application No. 61/981,421, filed Apr. 18, 2014. Application Ser. No. 14/048,635, filed on Oct. 8, 2013, is hereby incorporated by reference.

STATEMENT REGARDING FEDERALLY SPONSORED RESEARCH OR DEVELOPMENT

Not Applicable

BACKGROUND

1. Field of Invention

This invention pertains to a cotton sampling system. More particularly, this invention pertains to an automated sampling system that receives cotton samples, transports the samples for sub-sampling, and then transports the sub-samples for sample testing.

2. Description of the Related Art

The U.S. Department of Agriculture's (USDA) Agricultural Marketing Service (AMS) administers programs that facilitate the efficient, fair marketing of U.S. agricultural products, including food, fiber, and specialty crops. One of the programs of the Cotton and Tobacco Programs (C&T) is the Grading and Classing program for cotton. The Grading and Classing program for cotton classifies cotton samples taken from full bales at gin locations and transported to designated testing laboratories. The objective of the Grading and Classing program for cotton is to facilitate interstate and foreign commerce in cotton by providing official quality determinations that aid in marketing. The USDA AMS accomplishes this objective by inspecting, identifying, and certifying that product quality is in accordance with official standards. The program determines the quality of the current crop and of the annual carryover. Cotton standardization ensures uniformity in grading and classing.

Grading and classing cotton is a labor intensive operation conducted within a short time after the crop is picked. Samples are taken from full bales at gin locations. The samples are then transported to a testing laboratory. There, the sample is identified and tested. Testing is done with fiber testing instruments. The various tests includes determining the color grade and the leaf grade of American Upland Cotton, the grades of American Pima Cotton, the fiber length, Length Uniformity Index, fiber strength, Micronaire, trash, and color. High Volume Instruments (HVI) are used for the classification of all Upland and American Pima cotton. Additionally, trash and color are determined by HVI equipment.

The testing laboratories operate under strict climate requirements for cotton testing of 70 degrees F., plus or minus 1 degree and 65 percent relative humidity, plus or minus 2 percent. The cotton fiber reacts to changes in moisture. Therefore, it is necessary to condition all samples to the testing laboratory environment prior to testing. It is common to use Rapid Conditioning Units (RCU) for active conditioning. The RCU is a mechanism that conveys trays of samples along an air plenum that has conditioned air that conditions the cotton quickly (usually in less than 15 minutes from start to finish). The samples then move to a laboratory where HVIs test the characteristics of fiber properties and the corresponding data is then made available for the cotton industry to use to market cotton worldwide. Each HVI has a cycle time, but depends upon an operator to manually retrieve the main cotton samples from plastic trays, pull three (3) sub-samples from each of those samples, and load those sub-samples into pre-determined locations on the HVI to test for fiber length, strength, uniformity, and Micronaire (fineness and maturity). In addition, the operator places the remainder of the main sample in a designated location on the HVI to test fiber color and trash content. These instruments are solely relied upon by USDA and the domestic and international cotton industries to provide accurate and timely classification data for the marketing stream. The test data is transmitted in real time, as samples are tested, to mainframe computers and made available to owners or agents of the cotton all over the world.

The USDA AMS is considered the world's leader in HVI testing and tests virtually every bale of cotton grown in the U.S. each year (approximately 15-18 million samples on average in a typical year). Speed, accuracy and efficiency are key components of the operation. The current system relies upon multiple operators to perform these tests. The human element, despite training and experience, is always susceptible to error and inefficiencies. For example, a human operator pulls multiple sub-samples from each primary sample. The sub-samples are susceptible to variations of size, location, transport and handling, and placement into the HVI equipment. These variations potentially affect the consistency and accuracy of the measurements.

BRIEF SUMMARY

According to one embodiment of the present invention a cotton acquisition and tracking system with an automated cotton sampling system is provided. The automated sampling system includes a loading station, a split-rail conveyor system, an imaging station, and a transfer or second station. A production assistant at the loading station transfers sample halves into pairs of slots on the split-rail conveyor system. The sample halves are conveyed to a set of cameras in the imaging station. After the sample halves are imaged, the sample halves are transferred at the transfer station from the split-rail conveyor to primary sample carriers on a second conveyor. The second conveyor moves the primary sample carriers to the sub-sampling station, where sub-samples are acquired. The primary sample carriers are then conveyed to a staging area, where another operator performs classification of the samples and then discards the sample halves. The empty sample carriers are then conveyed to the transfer station, where they await to be filled with new sample halves.

In another embodiment, the cotton sampling system includes a transport system that moves the primary sample halves from the loading station to the various testing and/or sub-sampler stations. The transport system includes at least one over/under conveyor in which the samples are pushed along a fixed bed either above the conveyor or below the conveyor. In this way, the sample halves can be retested by being transported to the beginning of the transport system. The over/under conveyor allows for staging the sample halves by allowing the sample halves to be carried along the full length of the over/under conveyor, in both directions.

The sub-sampling station includes a sample feed mechanism that feeds a sample half into a fiber extraction mechanism. In one embodiment the sample feed mechanism includes a pair of pressure hands, each having a group of picks for engaging the sample half. The pressure hands are part of a walking beam mechanism that continuously pushes the sample half against the fiber extraction mechanism. The fiber extraction mechanism includes a rotating drum with pucks that extract fibers from the sample half. In one such embodiment, the pucks have combs oriented in the same direction. After extracting fibers, the drum moves the pucks so that an air jet blows the fibers off the pucks. The fibers are then transported to a cotton containment mechanism.

The cotton containment mechanism ensures the quality of the sub-sample by preventing clumps of fibers from passing through the system. A clump is a tuft of cotton fibers that form an oversized mass. When collecting a sub-sample, a clump being added to the sub-sample may render the sub-sample unacceptable because the maximum acceptable mass of the sub-sample may be exceeded by the step increase of mass from the clump. Additionally, downstream clogs are avoided when clumps are not transported through the system. In one embodiment, the cotton containment mechanism has an orifice that captures the clump, which is then extracted manually. In another embodiment, the cotton containment mechanism is an automated cotton containment mechanism (ACCM) that includes a gate valve that captures the clump, a detector that senses the presence of the clump and actuates the gate valve and a downstream diverter valve. The gate valve opens, allowing the clump to pass, and the diverter valve is positioned to route the clump to a waste receptacle. The gate valve includes a gate that moves between a normal position and a dump position. The gate in the valve has an arrow-shaped end that moves inside the throat of the gate valve. In the normal position the point of the gate defines a gap with the inside sidewall of the throat. There is sufficient clearance for the fibers to pass without restriction. Clumps, on the other hand, are captured by the shape of the orifice defined by the gate and the valve throat. To release the captured clump, the gate moves to increase the opening of the throat so that the clump passes through the gate valve. The detector includes a light beam directed across the throat and a light sensor. When the light beam is blocked by the clump the sensor detects the condition and causes the gate valve and the diverter valve to operate.

After acquiring sub-samples from a sample, the sub-samples are conditioned and staged. When a test device is available, a sub-sample is transferred to the test device. After testing the sub-sample is discarded.

The two major groups of tests required for sample testing are performed independently. One group of tests includes the imaging process, such as performed by a color/trash module. The other group of tests includes Micronaire included as an automated function of the HVI length/strength measurement. The sample transport system carries and stages the sample halves and sub-samples in order to perform these two major tests in an efficient process with minimal operator interaction.

A production assistant (PA) places cotton samples onto the split-rail conveyor. The production assistant separates the two halves of each sample and places them on a cleated, indexing conveyor in locations identified by visual aids. These aids (lights, decals, etc.) assist the PA in the loading process by alerting him to perform essentially three functions: load, align, and scan. Once the sample halves are loaded the PA scans the sample bale tag, and that information is written to an RFID tag affixed to the conveyor to identify the sample as it moves through the system. When the two halves of the sample are properly loaded (as monitored by background suppression sensors and various digital sensors) and the RFID tag properly written, loading lights illuminate and the production assistant repeats the process with the next sample.

Concurrently, the fixed bed, dual track indexing conveyor, driven by a servo-motor programmed to move in a specific manner given certain system clearances, will move the sample halves along the bed and position the sample halves in a series of imaging components comprised of upper and lower imaging devices or cameras. A unique split rail conveyor system with a window design allows for the simultaneous imaging of both the top and bottom of the sample halves. After the imaging of the first sample half is completed, the conveyor indexes a half-step to allow for the imaging of the second sample half. Other embodiments simultaneously image both sample halves at the same time, resulting in increased system efficiencies.

After imaging both sample halves, a batch-step of the conveyor system positions the imaged sample halves in a transfer station. Programmed movements coordinated with the PA and imaging processes moves the samples to a loading area. The sample halves are then loaded in primary sample carriers (PSCs), the sample bale tag information is written to identifying sample RFID tags associated with the PSC, and the imaged samples then continue to be processed through the rest of the system.

One embodiment of the transfer station has the sample halves pushed across the split-rail conveyor by pushers affixed to pneumatic actuators, through loading chutes, and into loading or flipper boxes. In one embodiment, the loading boxes rotate in a cascading motion and the samples are pressed on their sides into the PSC by forks also affixed to pneumatic actuators. The placement of the samples on their sides allows for better controlled sub-sampling.

The automated cotton sampling system includes a sub-sampling station, a sub-sample staging mechanism, and test devices. At the sub-sampling station the primary sample is positioned at a sub-sampling mechanism that removes a quantity of fibers and transports them to an indexer where a sub-sample is collected and conditioned. From there the sub-sample moves to a sub-sample staging device. In one embodiment, the fibers are removed from the primary sample by an extraction drum, with the fibers transported in a vacuum pneumatic system. In this way the sub-sample is collected with minimal fiber damage and with consistency between sub-samples.

During and after fiber removal and collection of the sub-sample, the sub-sample is conditioned with air at a selected temperature and with a selected relative humidity. After conditioning, the sub-sample is transferred to test station one, which can be a high volume instrument for testing cotton. In some cases the sub-sample is held in a staging area, such as a carousel, until the test station is ready to process the sub-sample. The sub-samples are transported through a vacuum pneumatic system. In this way, the needs for conditioning are reduced over conventional use of a rapid conditioning unit (RCU), thereby reducing power requirements and sample preparation time.

BRIEF DESCRIPTION OF THE SEVERAL VIEWS OF THE DRAWINGS

The above-mentioned features will become more clearly understood from the following detailed description read together with the drawings in which:

FIG. 2 is a perspective view of one embodiment of a primary sample carrier.

FIG. 3 is a front view of the embodiment of the primary sample carrier shown in FIG. 2.

FIG. 4 is a left side view of the embodiment of the primary sample carrier shown in FIG. 2.

FIG. 5 is a bottom view of one embodiment of a primary sample carrier.

DETAILED DESCRIPTION

Apparatus for a cotton acquisition and tracking system, or cotton sampling system, 100 is disclosed. Cotton samples 102 undergo multiple tests in an automated system 100. Various components and devices are generally indicated with a reference number and particular embodiments and variations are shown in the figures and described below have an alphabetic suffix, for example, the three-way valves are referred generically as item 714 and the individual valves are referenced as items 714-A, 714-B. Another example is the sub-sample staging device 108 that is depicted in three embodiments 108-A, 108-B, 108-C.

Figure 1:
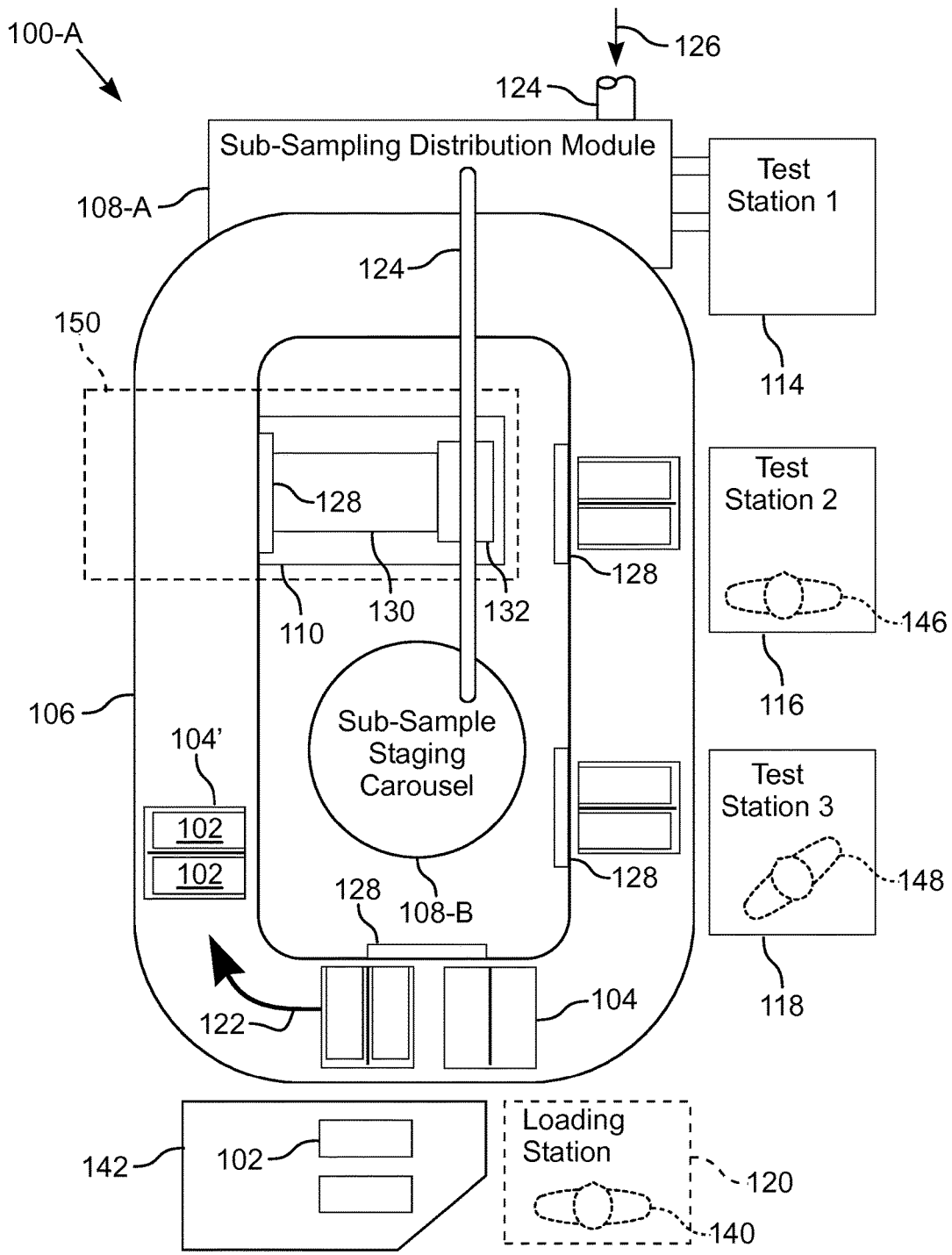
FIG. 1 is a plan view of one embodiment of a cotton acquisition and tracking system.

FIG. 1 illustrates a plan view of one embodiment of a cotton acquisition and tracking system 100-A. The system 100-A includes a conveyor 106 that loops between the various stations 120, 150, 116, 118. The illustrated embodiment of the sampling system 100-A shows only a single one of each of the various stations 120, 150, 116, 118. Other embodiments have multiple stations 120, 150, 116, 118. For example, with a 24 second cycle time for a single primary sample 102, the sampling system 100-A can accommodate six test stations one 114, where test station one 114 is a cotton testing instrument such as a high volume instrument. That is, the system 100-A is scalable to accommodate multiple test stations, depending upon the throughput of the sub-sampler station 150.

In the illustrated embodiment, at the loading station 120 is a table 142 that holds the cotton samples 102 to be tested. In other embodiments, the table 142 is instead a conveyor that transports the samples 102 to the loading station 120. A production assistant (PA) 140 operates the loading station 120. The production assistant 140 prepares the samples 102 by placing a pair of sample halves 102 into a primary sample carrier (PSC) 104 on the conveyor 106. That is, a sample 102 from a single bale is divided into halves, which are processed as a pair. In one embodiment, the production assistant 140 manually scans the bale identification tag of the sample 102 associated with a bale that is loaded into a primary sample carrier 104'. In one such embodiment, the bale tag identifier is written to a radio frequency identity (RFID) tag 406 associated with a primary sample carrier 104'. In another embodiment, the loaded primary sample carrier 104' passes by a scanner 128 near the loading station 120.

In another embodiment of the loading station 120, the operation is automated. The production assistant 140 loads the primary sample halves 102 directly to a tabulated indexing belt conveyor, which moves and positions the two half-samples 102 and associated bale tag 402, 404 at an Auto-Loading station. The two halves of the sample 102 are then automatically transferred to the primary sample carrier 104 and the bale tag information is recorded to the identifiers on the primary sample carrier 104. As the primary samples are moved to the primary sample carrier 104, a Load Assist mechanism deploys to insure the samples are constrained within the primary sample carrier 104 during loading. The primary sample carrier 104 moves to and is then processed by the sub-sampler.

In another embodiment, the primary sample is loaded by the production assistant 140 directly to a tabulated indexing belt conveyor, which moves and positions the two half-samples 102 and associated identifying bale tag 402, 404 at an Imaging System. The cameras automatically move into position above and below each half of the primary sample carrier 104 to capture two images of each half of the primary sample 102, and capture and store the bale tag information. Once the imaging is complete, the primary sample 102 moves to the Auto-Loading station described above. The bale tag information captured by the Imaging System is then transferred to the primary sample carrier identifying tags 402, 404.

In yet another embodiment, the primary sample 102 moves directly to the sub-sampler 150, such as through a fixed chute or other assembly that maintains traceability of the primary sample 102. In such an embodiment, the conveyor 106 and primary sample carrier 104 are not necessary for transporting the primary sample 102 from the loading station 120 to the sub-sampler 150.

The conveyor 106 moves in a direction 122 to transport the loaded primary sample carrier 104' to the sub-sampler station 150. A scanner 128 at the sub-sampler station 150 identifies the loaded primary sample carrier 104'. The conveyor 106 then transports the loaded primary sample carrier 104' to the color/trash station 116 for the person 146 manning test station two 116. A scanner 128 at test station two 116 identifies the loaded primary sample carrier 104'. The conveyor 106 then transports the loaded primary sample carrier 104' to test station three 118. A scanner 128 at test station three 118 identifies the loaded primary sample carrier 104' for the person 148 manning test station three 118. At test station three 118 the samples 102 are removed from the primary sample carrier 104 and the empty primary sample carrier 104 returns to the loading station 120 for the next sample 102 to be inserted.

The sub-sampler station 150 includes a sub-sampler module 110. In the illustrated embodiment, a second conveyor 130 moves a loaded primary sample carrier 104' to the sub-sampling mechanism 132. The sub-sampler mechanism 132 extracts a sub-sample 102-SS from the sample 102. FIG. 1 illustrates two alternative embodiments for handling the sub-samples 102-SS. The first embodiment includes moving the sub-sample 102-SS from the sub-sampler mechanism 132 to the sub-sampling distribution module 108-A, where the sub-samples 102-SS are staged until they are moved to test station one 114, where the sub-samples 102-SS are tested, such as with a high volume instrument (HVI). In this embodiment, the sub-samples 102-SS are temporarily held in a carrier, such as two plates with a sub-sample carrier 802 sandwiched therebetween or a sample carrier 104 carrying at least one sub-sample carrier 802 with the carrier 104 having perforations located such that conditioning air is circulated through the sub-sample carrier 802. The sub-sampling distribution module 108-A receives conditioned air 126 through an inlet port 124. The conditioned air 126 is routed to the sub-sampler module 110. The conditioned air 126 is suitable for conditioning the sub-sample for testing.

In the other embodiment, the sub-sample 102-SS from the sub-sampler 132 is moved through the pneumatic system 124 to the sub-sample staging carousel 108-B, where the sub-samples 102-SS are stored in a conditioned environment until the sub-samples 102-SS are moved through the pneumatic system 124 to test station one 114, where the sub-samples 102-SS are tested.

FIG. 2 illustrates a perspective view of one embodiment of a primary sample carrier 104-A. FIG. 3 illustrates a front view of the embodiment of the primary sample carrier 104-A shown in FIG. 2. FIG. 4 illustrates a left side view of a primary sample carrier 104.

The primary sample carrier 104 is a box-like structure that has a pair of sidewalls 202, a base 208, a divider 206, and a rear plate, or sub-sampling plate 204. Each sidewall 202, the divider 206, the base 208, and sub-sampling plate or wall 204 define a space dimensioned to receive one half of the pair of primary samples 102. The upper portion of the sidewalls 202 are angled away from the interior to aid in the insertion of the primary sample 102.

The rear of the primary sample carrier 104 is a sub-sampling plate 204. In the embodiment illustrated in FIGS. 2 and 3, the sub-sampling plate or wall 204-A has a series of openings or holes 214 through which a portion of the primary sample 102 protrudes when the sample 102 is pushed against the sub-sampling plate 204-A.

The illustrated embodiment of the primary sample carrier 104 is configured to have a permanent identifier 402 and a holder for a bale tag 404. The identifiers and tags 402, 404 are read by the scanners 128. A pair of permanent identifiers 402 are attached to the carrier 104 at the upper portion of each sidewall 202. The placement of the permanent identifiers 402 on the underside of the angled upper portion of the sidewalls 202 provides protection of the permanent identifiers 402 as the primary sample carriers 104 move on the conveyor 106. In this way, the likelihood of damaging the identifiers 402 is reduced. In the illustrated embodiment, a pair of identifiers 402 are provided for redundancy in case one identifier 402 is damaged such that the identification code on one identifier 402 cannot be read.

In the illustrated embodiment, a bale tag 404 corresponding to the primary sample 102 carried in the carrier 104 is attached to one sidewall 202. In one such embodiment, the bale tag 404 is inserted through a slot 212 in the canted portion of the sidewall 202 and into a holder on the outside of the sidewall 202. In another such embodiment, a second slot 214 in the sidewall is positioned to allow automatic extraction of the bale tag 404.

In one embodiment, the identifiers and tag 402, 404 are tags with bar codes that are read by bar code readers in the scanners 128. In other embodiments, either the permanent identifiers 402 or separate tags 406 are radio frequency identity (RFID) tags or other type of re-writable, machine readable tags. In such an embodiment, the RFID tags 402, 406 are written with a code associated with the identification code of the bale tag 404. The bale tag 404 is then placed in the carrier 104 with the primary sample 102. The scanners 128 read the RFID tag 402, 406 to identify the specific primary sample 102 in the carrier 104.

FIG. 5 illustrates a bottom view of another embodiment of a primary sample carrier 104'. The carrier 104' has a pair of windows 502 in the bottom 208. The windows 502 provide a view of the primary sample 102 in the carrier 104' for imaging, such as is performed at a color/trash station, such as test station two 116. In another embodiment, an automated imaging system uses the windows 502 to capture an image of the bottom of the sample 102 in the carrier 104'. The top of the carrier 104' is open, thereby allowing an image of the top of the sample 102 to also be captured.

Figure 6:
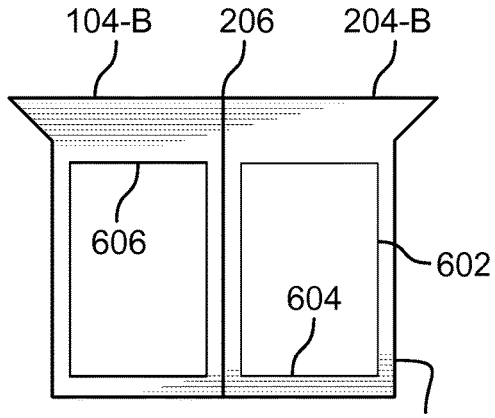
FIG. 6 is a front view of another embodiment of the primary sample carrier.

FIG. 6 illustrates a front view of another embodiment of the primary sample carrier 104-B. In the illustrated embodiment, the back wall 204-B includes a pair of windows 602. Each half of the cotton sample 102 has its own window 602. In this way, a sub-sample 102-SS is obtainable from each half of the cotton sample 102.

Each window 602 has a lower edge 604 and an upper edge 606. The lower edge 604 is elevated relative to the base 208. In this way, when the extraction drum 702 is rotating in a direction that is forcing the sample 102 toward the lower edge 602, the sample is restrained from being drawn out of the primary sample carrier 104-B. The motion of the drum 702 relative to the sample 102 forces the sample 102 toward the base 208 and sample 102 catches or is restrained at the portion of the back wall 204-B between the base 208 and the lower edge 604 of the window 602. The height of the window 602 is dimensioned such that the back wall 204-B above the upper edge 606 restrains the sample 102 when the motion of the drum 702 relative to the sample 102 forces the sample 102 away from the base 208.

Figure 7:
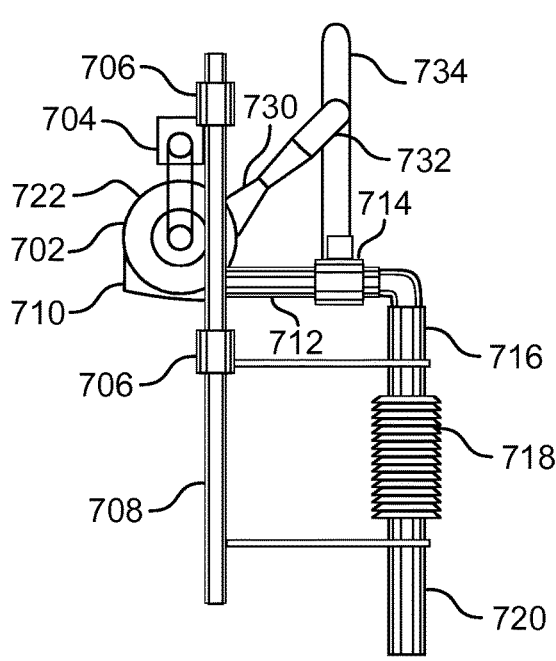
FIG. 7 is a side view of one embodiment of a sub-sampler mechanism.

FIG. 7 illustrates a side view of one embodiment of a sub-sampler mechanism 132-A. Because the primary sample carrier 104 carries a pair of cotton sample halves 102, the sub-sampler mechanism 132-A includes a pair of drums 702, one for each one of the pair of sample halves 102. In one embodiment, the sub-sampler mechanism 132-A has the capability of processing two loaded primary sample carriers 104' to produce two pairs of sub-samples 102-SS at one time.

The illustrated embodiment of the sub-sampler mechanism 132-A includes an extraction drum 702 that moves vertically to engage the sample 102 protruding from the sub-sampling plate 204-A. The extraction drum 702 rotates reciprocally by a motor 704. The extraction drum 702 also moves vertically along the vertical supports 704 such that the extraction drum 702 engages the full height of the sub-sampling plate 204-A. Sleeve bearings 706 maintain alignment of the extraction drum 702 with the sub-sampling plate 204-A such that the card pucks 722 on the extraction drum 702 engage the portion of the primary sample 102 protruding from the openings 214 in the sub-sampling plate 204-A. In another embodiment, the sub-sampler mechanism 132-A is stationary and the extraction drum 702 engages the primary sample 102 through the windows 602 in the sub-sampling plate 204-B of the primary sample carrier 104-B.

Figure 10:
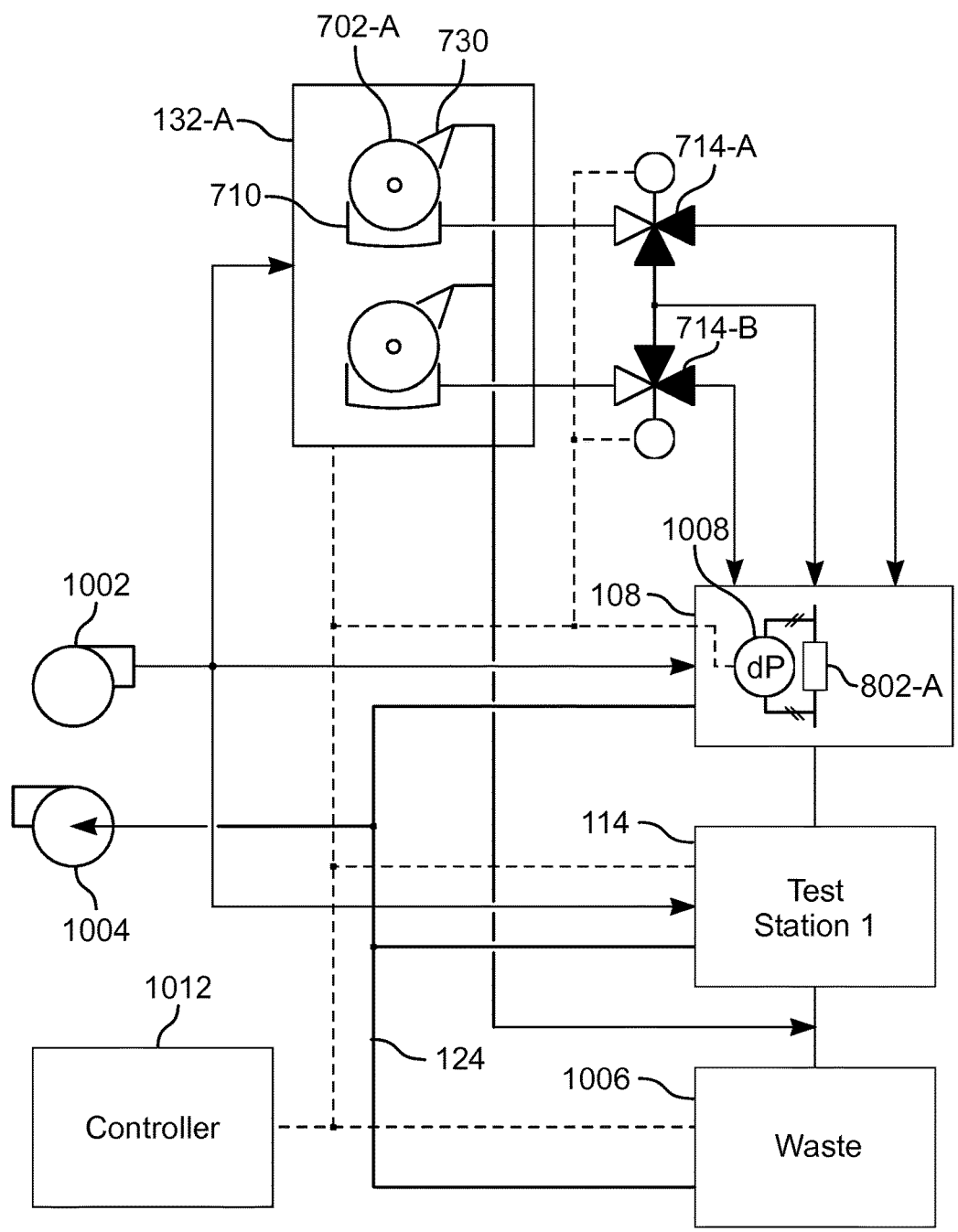
FIG. 10 is a simplified piping and instrumentation diagram of a sampling system with the embodiment of the sub-sampling mechanism shown in FIG. 7.

Under the extraction drum 702 is a shroud or vacuum nozzle 710 connected to a vacuum pipe or line 712. The vacuum line 712 is connected to a three-way valve 714 that is also connected to a second pipe 716 that is connected to a bellows 718. The bellows 718 allows for the shroud 710, the vacuum line 712, the valve 714, and the second pipe 716 to move vertically with the extraction drum 702 while the sample discharge pipe 720 remains stationary. The bellows 718 maintains the air-tightness of the pneumatic system 124 as the extraction drum 702 moves during the sub-sample collection. As seen in FIG. 10, the third connection to the three-way valve 714 is connected to a tee 722 that connects the three-way valves 714 associated with each of the pair of extraction drums 702 associated with each one of the pair of primary samples 102 in the carrier 104. The tee is connected to another second pipe 716 that is connected to another bellows 718 connected to another discharge pipe 720. In this way, a sub-sample 102-SS is collected from each of the pair of primary samples 102 or, alternatively, a single sub-sample 102-SS is collected from fibers of the pair of primary samples 102. In another embodiment, only one sample 102-SS is collected from each extraction drum 702 and the third connection is not needed.

After the required amount of fibers are removed and sent to the sub-sample carrier 802, all the fibers on the card cylinder must be removed to avoid contaminating other sub-samples 102-SS. A doffer 730 engages the extraction drum 702 to clean any remaining fibers from the puck 722 on the extraction drum 702. The doffer 730 is connected to a manifold 732 that is connected to a vacuum line 734 that carries the unneeded removed fibers for disposal.

The sub-sampler mechanism 132-A collects sub-samples by moving the puck 722 against the primary sample 102. The fibers removed from the primary sample 102 are doffed from the puck 722 and collected in the shroud 710 where they are transported through the vacuum line 712. In one embodiment, air jets directed toward the puck 722 assist in removing the fibers from the extraction drum 702. Depending upon the position of the three-way valve 714, the fibers are either pulled through the sub-sample discharge pipe 720-A or combined with the fibers from the other one of the pair of the primary sample as they are pulled through the sub-sample discharge pipe 720.

Figure 8:
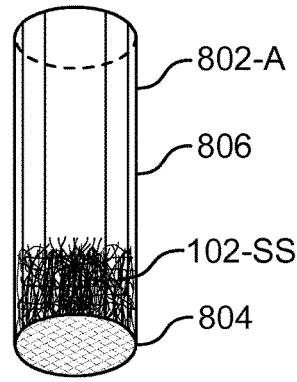
FIG. 8 is a perspective view of one embodiment of a sub-sample carrier.

FIG. 8 illustrates a perspective view of one embodiment of a sub-sample carrier 802-A. The sub-sample carrier 802-A is configured to be positioned in the flow stream of the vacuum pneumatic system 124. For example, the sub-sample carrier 802-A is mounted in a carrier between two plates with the carrier positionable so that each sub-sample 102-SS can be captured in a specific one of a sub-sample carrier 802-A. For example, the staging carrier 108-B includes a plurality of sub-sample carriers 802-A for storing sub-samples 102-SS before testing. In this way the flow of sub-samples 102-SS accommodates the vagaries of the sub-sampler 150 and the test station 114 to ensure a steady supply of sub-samples 102-SS to maximize efficiency of the test station 114.

The sub-sample carrier 802-A includes a hollow cylinder or tube 806 with one end having a fine mesh screen 804. In one embodiment, the hollow cylinder 806 is an acrylic tube. The fibers are pulled through the pneumatic system 124 and deposited into the sub-sample carrier 802-A against the screen 804 at the bottom of the tube 806. The sub-sample 102-SS is formed from the collected fibers.

The weight of the fibers making up the sub-sample 102-SS is determined with the sub-sample 102-SS in the sub-sample carrier 802-A. In one embodiment, the differential pressure is measured across the sub-sample 102-SS collected at the screen 804. The differential pressure across the sub-sample 102-SS correlates to the weight of the sub-sample 102-SS, which is desired to be between 8 and 15 grams.

Figure 9:
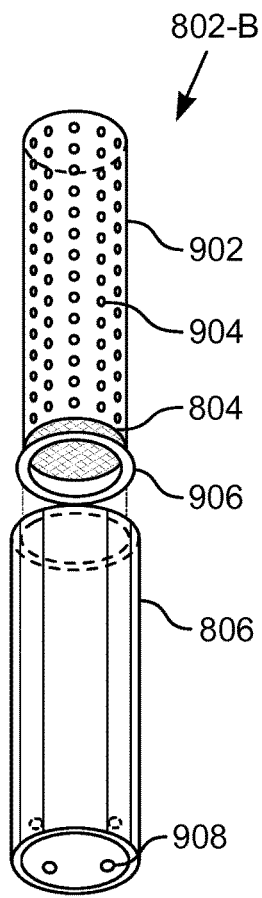
FIG. 9 is a perspective view of another embodiment of a sub-sample carrier.

FIG. 9 illustrates a perspective view of another embodiment of a sub-sample carrier 802-B. The sub-sample carrier 802-B is a vortex accumulation chamber that is configured to be positioned in the flow stream of the vacuum pneumatic system 124. For example, a plurality of sub-sample carriers 802-B are mounted in the carousel 108-B so that each sub-sample 102-SS can be captured in a specific one of a sub-sample carrier 802-A. In another embodiment the sub-sample carriers 802-B are included in an indexer 1312 that collects and conditions sub-samples 102-SS before moving them to a staging device like the carousel 108-B or directly to testing device 114. The double-walled configuration of the carrier 802-B facilitates the flow of conditioned air through the fibers, thereby aiding conditioning of the collected sub-sample 102-SS within a short time period.

The sub-sample carrier 802-B includes an outer hollow cylinder or tube 806. The carrier 802-B also includes an inner hollow cylinder 902 with one end having a fine mesh screen 804. The sides of the inner hollow cylinder 902 have a series of openings 904 spaced along the cylindrical surface. The inner hollow cylinder 902 is held in fixed relation to the outer hollow cylinder 806. In one embodiment, the two cylinders 806, 902 are positioned between two plates with coaxial openings.

In one embodiment, the two cylinders 806, 902 are acrylic tubes. In operation, a vacuum from the pneumatic system 124 is applied to the screen 804 and the open end of the outer hollow cylinder 806 that is proximate the screen 804. In this way, air enters the end of the inner hollow cylinder 902 opposite the mesh 804. The air flows through the multitude of openings 904 and the mesh 804, thereby depositing or trapping the fibers from the sub-sampler mechanism 132 against the inner sidewall of the inner hollow cylinder 902 and against the screen 804 at the bottom of the tube 902. The sub-sample 102-SS is formed from the collected fibers.

The weight of the fibers making up the sub-sample 102-SS is determined with the sub-sample 102-SS in the sub-sample carrier 802-B. In one embodiment, the height of the fibers in the inner hollow cylinder 902 is measured, such as with an optical sensor 1304. The height of the fibers in the tube 902 correlates to the weight of the sub-sample 102-SS, which is desired to be between 8 and 15 grams.

A circular valve 906 is positioned adjacent the mesh 804. The valve 906 is a one-way valve that permits air to flow from the space between the two cylinders 806, 902 out the bottom of the sub-sample carrier 802-B and prevents air from flowing from the bottom of the carrier 802-B into the space between the two cylinders 806, 902. In this way, the flow of conditioning air is facilitated during the storage phase, and, during the sub-sample extraction phase the extraction of the sub-sample is facilitated by directing the positive air pressure only through the inner cylinder 902. In various embodiments, the valve 906 is a reed-type valve or a flapper-type valve that permits air flow in only one direction. In the illustrated embodiment, the valve 906 is a ring of flexible sheet-like material. The valve 906 has a central opening to accommodate the mesh 804. The outer cylinder 806 has a plurality of nubs 908 on the inside surface that are positioned adjacent the bottom of the inside cylinder 902. The valve 906 is positioned at the bottom of the inside cylinder 902 adjacent the mesh 804, and the upper surface of the valve 906 is proximate the bottom surface of the nubs 908. In this way air flow through the valve 906 and the area between the two cylinders 806, 902 is permitted in the direction toward the mesh through the cylinders 806, 902, but is inhibited in the opposite direction. In this way a puff of air to discharge the sub-sample 102-SS from the carrier 802-B is limited to entering only the inner cylinder 902 of the carrier 802-B at the mesh 804. In one such embodiment, the nubs 908 also serve to secure the inner cylinder 902 inside the outer cylinder 806.

FIG. 10 illustrates a simplified piping and instrumentation diagram of a sampling system 100 with one embodiment of a sub-sampling mechanism 132-A. The pneumatic system 124 includes an air pump 1002 that supplies conditioned air to the sub-sampling mechanism 132-A, the sub-sample staging device 108-A, 108-B, and test station one 114. The conditioned air from the air pump 1002 is directed toward the portion of the system 100 where the sub-sample 102-SS passes. The air is conditioned to maintain a specified temperature and relative humidity to condition the sub-samples 102-SS.

The pneumatic system 124 also includes a vacuum pump 1004 connected to the sub-sample staging device 108-A, 108-B, test station one 114, and the waste device 1006. The vacuum pump 1004 is selectively connected to various pipes and equipment to pull the fibers or the sub-sample 102-SS from one location to another within the pneumatic system 124. For example, the vacuum from the vacuum pump 1004 is used to pull the fibers from the extraction drum 702-A, through the three-way valve 714-A, and to the staging device 108, where the sub-sample 102-SS is held until test station one 114 is ready to test the sub-sample 102-SS.

A controller 1012 is connected to the three-way valves 714, the sub-sampling staging device 108, which may include an indexer-type device 1312, test station one 114, and the waste device 1006. The differential pressure sensor 1008 is connected across a sub-sample carrier 802-A to determine if the sub-sample 102-SS is within weight limits. The controller 1012 monitors the measured differential pressure sensor 1008 and controls the sub-sampling mechanism 132-A and three-way valves 714 to collect more fibers until the desired volume or mass of the sub-sample 102-SS is obtained. In another embodiment the sensor 1008 is an optical sensor that detects a quantity of fibers in the carrier 802-A. In another embodiment, the sub-sample carrier 802-B is of the double-walled configuration, which provides enhanced conditioning capabilities, thereby shortening the conditioning time. The controller 1012 monitors test station one 114 and initiates the removal of a tested sub-sample 102-SS and the transfer of the next sub-sample 102-SS to be tested from the staging device 108. For example, the controller 1012 operates various valves in the pneumatic system 124 to pull the desired sub-sample 102-SS from the staging device 108 to test station one 114.

In one embodiment, the controller 1012 monitors the waste device 1006 to determine if the discarded sub-samples 102-SS need to be removed from the waste device 1006.

As used herein, the controller 1012 should be broadly construed to mean any device that accepts inputs and provides outputs based on the inputs, for example an analog control device or a computer or component thereof that executes software. In various embodiments, the controller 1012 is one of a specialized device or a computer for implementing the functions of the invention. The controller 1012 includes input/output (I/O) units for communicating with external devices and a processing unit that varies the output based on one or more input values. A computer-based controller 1012 includes a memory medium that stores software and data and a processing unit that executes the software. Those skilled in the art will recognize that the memory medium associated with the computer-based controller 1012 can be either internal or external to the processing unit of the processor without departing from the scope and spirit of the present invention.

The input component of the controller 1012 receives input from external devices, such as the differential pressure sensor 1008 and valve position sensors. The output component sends output to external devices, such as the three-way valves 112. The storage component stores data and program code. In one embodiment, the storage component includes random access memory and/or non-volatile memory.

The simplified piping and instrumentation diagram does not illustrate various connections and routings, however, those skilled in the art will recognize the need for such connections and routings and understand how to make such connections and routings, based on the components ultimately selected for use.

Figure 11:
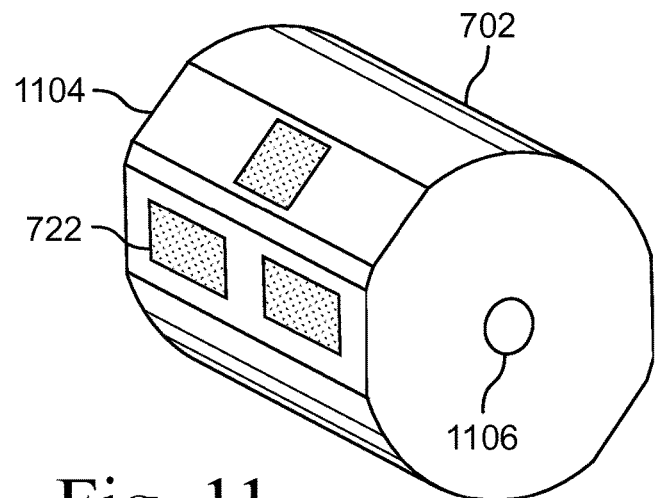
FIG. 11 is a perspective view of one embodiment of an extraction drum.
Figure 12:
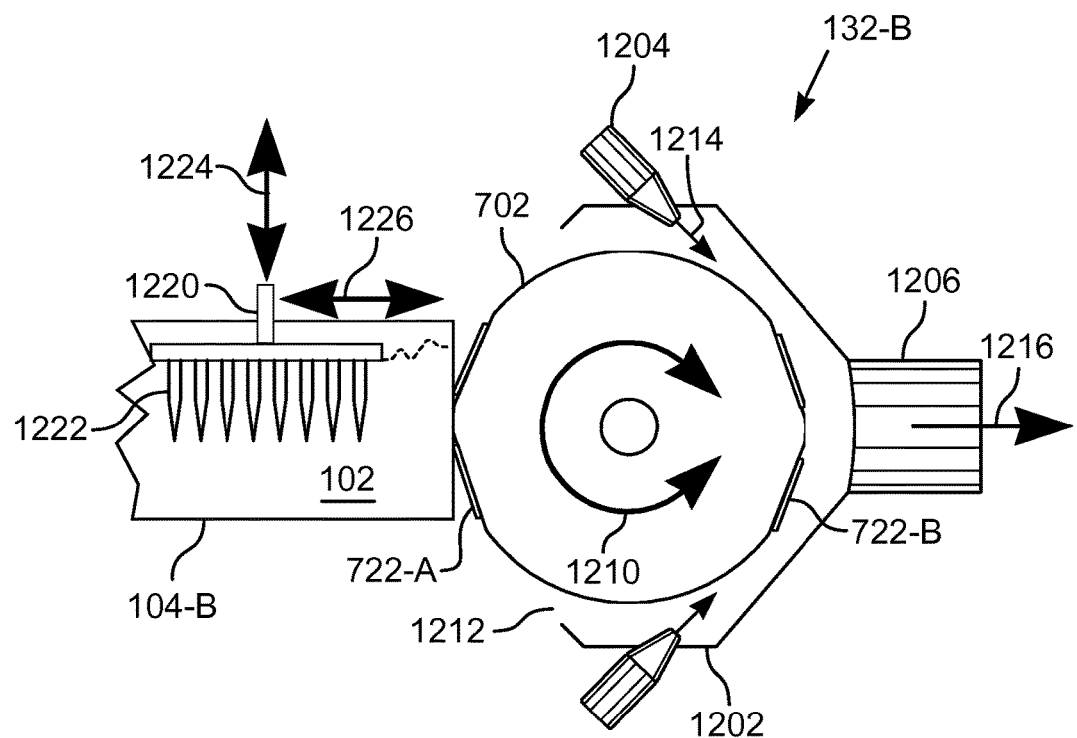
FIG. 12 is a symbolic side view of another embodiment of a sub-sampler mechanism showing the sample feed mechanism.

FIG. 11 illustrates a perspective view of one embodiment of an extraction drum 702. FIG. 12 illustrates a side view of another embodiment of a sub-sampler mechanism 132-B showing the sample feed mechanism 1220. The sub-sampler mechanism 132-B includes the extraction drum 702, the jets 1204, and the shroud 1202. The drum 702 is a cylinder that rotates 1210 about an axle 1106. The drum 702 is dimensioned to engage the window 602 in the primary sample carrier 104-B. Because the primary sample carrier 104-B has two windows 602, two drums 702 are positioned in tandem, side-by-side. Illustrated adjacent the drum 702 is a primary sample carrier 104-B holding a sample 102 that is engaged by a sample feed mechanism 1220 that moves in two axes 1224, 1226.

The sample feed mechanism 1220 includes a grid of picks 1222, which are needle-like protrusions configured to penetrate and grip the sample 102. The sample feed mechanism 1220 moves in two axes 1224, 1226. The first axis 1224 is perpendicular to the bottom of the primary sample carrier 104. The primary sample 102 defines a plane that is parallel to the bottom of the primary sample carrier 104 carrying that sample 102 and parallel to the axis of rotation 1210 of the drum 702. The second axis 1226 is parallel to the bottom of the primary sample carrier 104 and perpendicular to the axis of rotation 1210 of the drum 702.

In operation, the primary sample carrier 104 is moved toward the drum 702 with the pucks 722 engaging the sample 102 through the windows 602. The sample feed mechanism 1220 is positioned toward the end of the primary sample carrier 104 away from the windows 602. The feed mechanism 1220 is then lowered 1224 so that the picks 1222 engage the sample 102 securely. The feed mechanism 1220 moves in a direction 1226 toward the drum 702, thereby causing the sample 102 to engage the drum 702 through the window 602. The feed rate of the sample 102 is dependent upon the speed of the feed mechanism 1220 along the second axis 1226. When the feed mechanism 1220 reaches the end of its travel, which is near the windows 602, the feed mechanism 1220 moves upward 1224 and, when the picks 1222 clear the sample 102, backwards 1226 away from the windows 602. The feed mechanism 1220 re-engages the sample 102 when the mechanism 1220 is positioned toward the end of the primary sample carrier 104 away from the windows 602.

On opposite sides of the drum 702 are two pairs of flat sections 1104. Card pucks 722 are spaced apart on the flat sections 1104. In the illustrated embodiment, one flat section 1104 has two pucks 722 spaced apart and the other flat section 1104 has a puck 722 centered between the other two pucks 722. The card wire on the pucks 722 are aligned such that the pucks 722 grab fibers from primary sample 102 when the drum 702 rotates 1210 and moves the pucks 722 across the primary sample 102. The card wire on the pucks 722-B on the opposite side of the drum 702 are aligned in the opposite direction so that the pucks 722-B grab fibers when the drum rotates 1210 in the opposite direction.

On the side of the drum 702 opposite of where the primary sample 102 is positioned is the shroud 1202. The shroud 1202 encloses a portion of the drum 702 and includes an outlet 1206 through which the extracted fibers flow 1216. The pneumatic system 124 applies a vacuum to the shroud outlet 1206, causing air to flow from the gaps 1212 between the open end of the shroud 1202 and the drum 702. In addition, a plurality of jets 1204 are positioned above and below the drum 702. The jets 1204 direct air 1214 tangentially to the drum 702 to blow the fibers extracted by the pucks 722 when the pucks 722 rotate past the air stream 1214 from the jets 1204. The air flowing through the gap 1212 and the air stream 1214 from the jets 1204 dislodges the fibers from the pucks 722 and carries the fibers through the shroud 1202 and into the outlet 1206. The fibers pass through the pneumatic system 124 until the fibers reach the sub-sample carrier 802, where the fibers are collected as a sub-sample 102-SS.

In the illustrated embodiment, the drum 702 rotates with a reciprocal motion 1210. In one such embodiment the drum 702 rotates about an axis and pneumatic cylinders provide the motive force to rotate the drum 702 first in one direction and then in the opposite direction in order to create the reciprocal motion 1210. In another embodiment the reciprocal motion 1210 is created by servomotors that are controlled to rotate the drum 702. One feature of using the servomotor to reciprocate the drum 702 is that the amount of rotation in each direction can be greater than the amount from pneumatic cylinders. A large degree of rotary movement has the advantage of allowing the pucks 722 to be spaced further apart along the circumference, thereby avoiding the pulled fibers from accumulating on the pucks 722. The reciprocal motion 1210 allows one set of pucks 722-A to extract fibers from the primary sample 102 when the pucks 722-A rotate past the primary sample 102. As the pucks 722-A rotate past the jets 1204, the air stream 1214 from the jets 1204 blows the fibers off the pucks 722-A. The air stream from jets 1204 is timed to the rotation of the drum 702 to strike the pucks 722-A as puffs of air sufficient to dislodge the fibers from the card wire on the pucks 722-A. The drum 702 includes timing marks that trigger the puffs of air from the jets 1204. In this way the air jets serve to dislodge fibers without blowing the fibers around the drum 702 and out the opposite gap 1212. That is, the air stream from the jets 1204 are timed synchronously with the radial location of the pucks 722 relative to the extraction manifold or shroud 1202 and outlet 1206. After the pucks 722-A pass through the air stream 1214, the drum 702 changes direction 1210. When the pucks 722-A move across the primary sample 102 as the pucks 722-A return to their starting position, any remaining fibers on the pucks 722-A is removed by the rubbing of the primary sample 102 against the pucks 722-A. Upon reaching the starting position, the drum 702 changes direction 1210, again.

The pucks 722-B on the opposite side of the drum 702 operate in a similar manner, but 180 degrees out of phase with the other set of pucks 722-A. That is, when the drum 702 is rotated for the first set of pucks 722-A to extract fibers from the primary sample 102, the opposite set of pucks 722-B will move across the primary sample 102 so that the remaining fibers are removed from the pucks 722-B. With the pucks 722-A, 722-B oriented to extract and remove fibers as the drum 702 reciprocates in both directions 1210, the efficiency of the sub-sampling mechanism 132-B is increased.

In another embodiment both sets of pucks 722-A, 722-B have combs oriented such that fibers are pulled from the sample 102 when the drum 702 rotates in one direction 1210. In such an embodiment only one set of jets 1204 (either upper or lower, depending upon the direction of the pucks 722) is needed because the same air jet 1204 blows off the collected fibers from both sets of pucks 722-A, 722-B.

Figure 13:
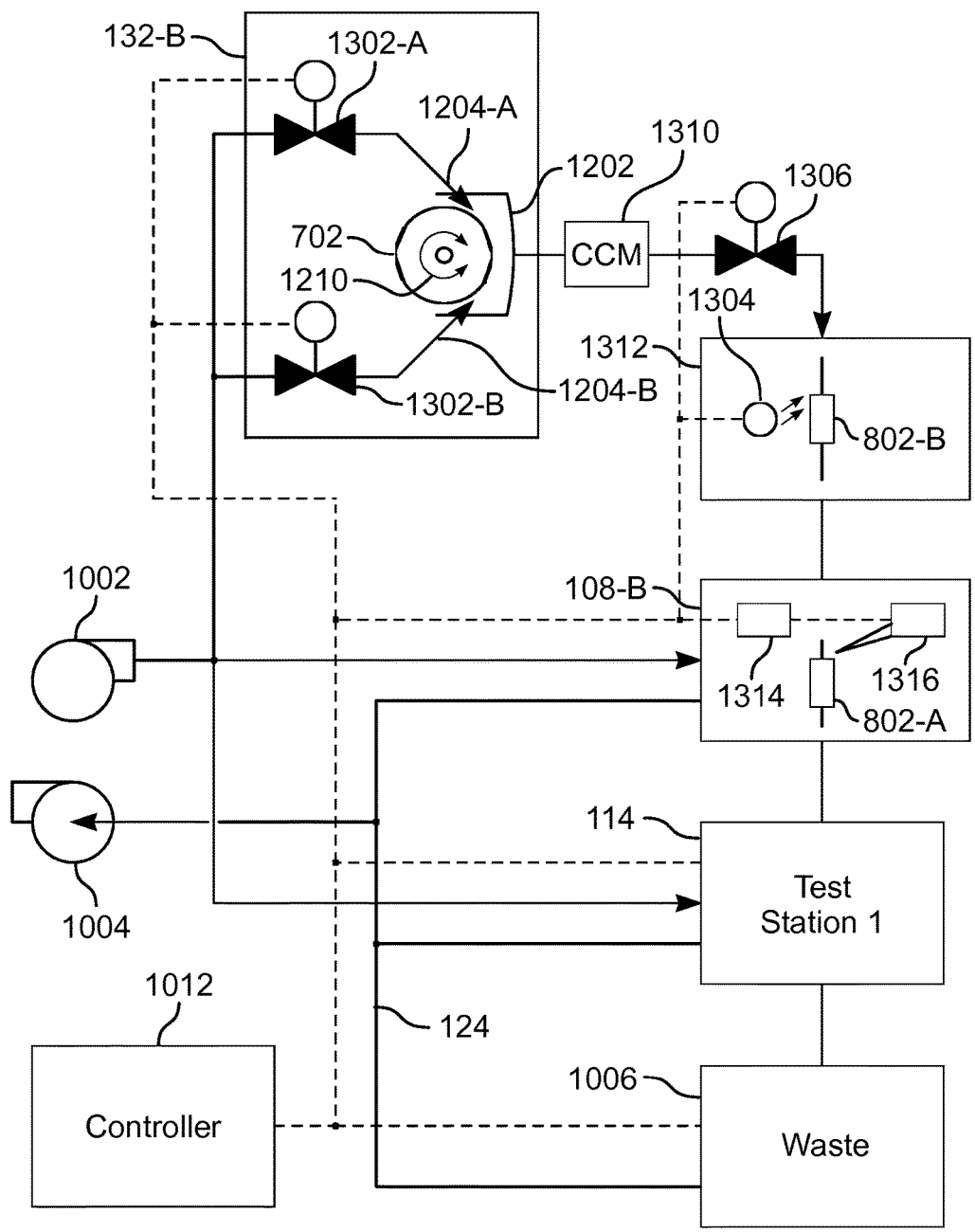
FIG. 13 is a simplified piping and instrumentation diagram of a sampling system with the embodiment of the sub-sampling mechanism shown in FIG. 12.

FIG. 13 illustrates a simplified piping and instrumentation diagram of a sampling system 100 with another embodiment of a sub-sampling mechanism 132-B. The illustrated sub-sampling mechanism 132-B employs the extraction drum 702 illustrated in FIGS. 11 & 12. Only a single drum 702 is illustrated. For the primary sample carrier 104-B illustrated in FIG. 6, a pair of drums 702 are used with the drums 702 side-by-side. In various embodiments, multiple sets of drums 702 are used based on the number of sub-sampler stations 150 in the cotton acquisition and tracking system 100.

A cotton containment mechanism (CCM) 1310 is located in the vacuum tubes downstream from the sub-sampling mechanism 132-B. The CCM 1310 prevents oversized masses of cotton fibers from flowing to the downstream components. In one embodiment, the CCM 1310 is a manual mechanism that detects a clump or oversized mass and allows for an operator to remove the clump or oversized mass. In another embodiment, the CCM 1310 is an automated mechanism that removes the clump or oversized mass without operator intervention.

Figure 18:
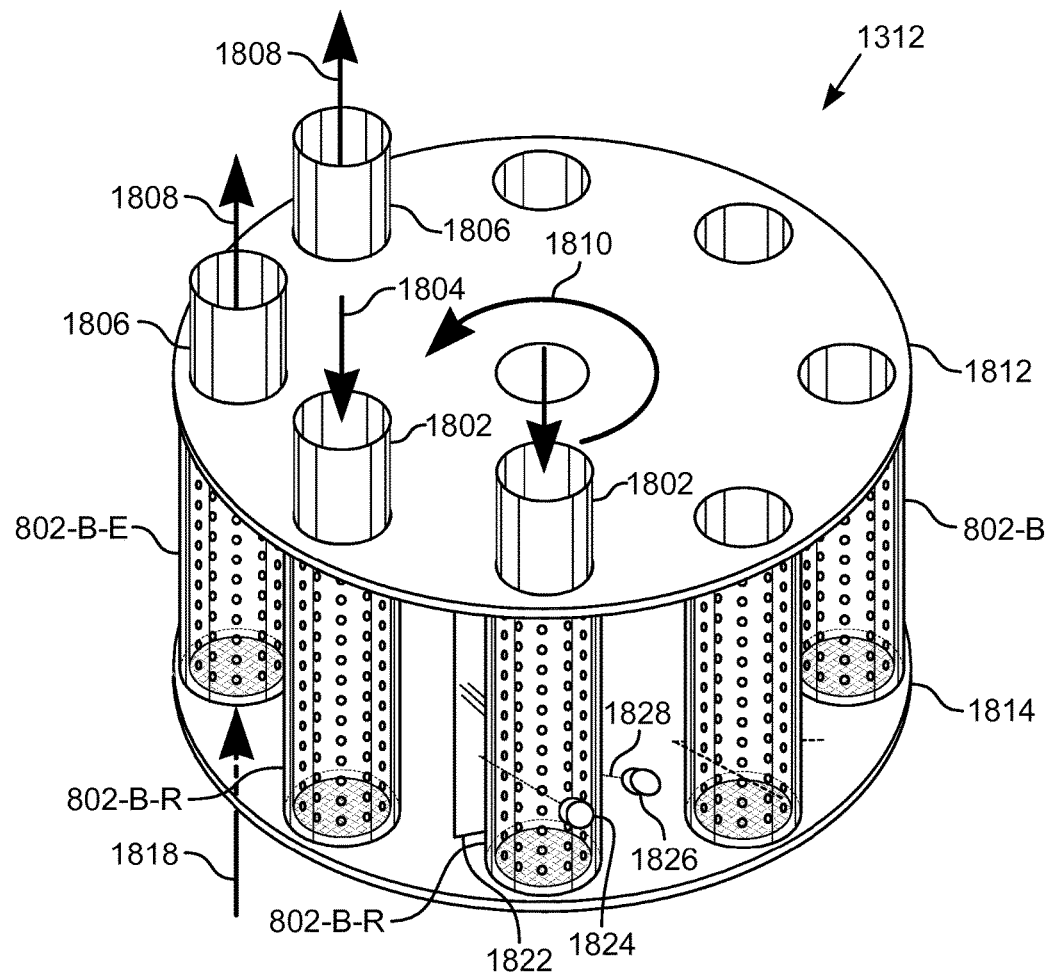
FIG. 18 is a perspective view of one embodiment of an indexer using the embodiment of the sub-sample carrier shown in FIG. 9.

The outlet of the cotton containment mechanism 1310 is directed to an indexer 1310, which provides sub-samples 102-SS to the sub-sample staging carousel 108-B. The indexer 1312 includes a plurality of sub-sample carriers 802-B, such as is shown in FIGS. 9 and 18. The illustrated embodiment shows an optical sensor 1304 that detects the presence of sufficient fibers for a sub-sample 102-SS. In various embodiments the sensor 1304 can measure various parameters, such as differential pressure, that indicate when sufficient fibers have been collected in the sub-sample carrier 802-B.

The outlet of the indexer 1310 is directed to a sub-sample staging carousel 108-B. The staging carousel 108-B stores sub-samples 102-SS in sub-sample carriers 802-A until such time that they are needed by the test station 114. Each sub-sample 102-SS in the carousel 108-B is associated with an identification device 1314. In one embodiment, the identification device 1314 is a writeable RFID that stores the sample identification code associated with the sub-sample 102-SS. The sub-samples 102-SS are loaded into empty sub-sample carriers 802-A and expelled from loaded sub-sample carriers 802-A by a combination of a rotary storage unit similar to that of the indexer 1312 and a swing arm 1316 that connects the pneumatic tubing to a selected sub-sample carrier 802-A. In operation, when receiving a sub-sample 102-SS, the carousel 108-B moves to an empty sub-sample carrier 802-A, thereby connecting the pneumatic system to the sub-sample carrier 802-A, which receives the sub-sample 102-SS. The carousel 108-B also writes the sample identification code to the identification device 1314. After receiving the sub-samples 102-SS the carousel 108-A rotates to move the newly loaded carriers 802-A away from the pneumatic tubing that delivered the sub-samples 102-SS and positions empty sub-sample carriers 802-A to receive the next sub-samples 102-SS. In this way the loaded carriers 802-A are positioned for the swing arm 1316 to extract the sub-samples 102-SS without requiring the carousel 108-B to move.

When a sample is to be removed, the swing arm 1316 moves to a full or loaded sub-sample carrier 802-A, thereby connecting the pneumatic system to the selected sub-sample carrier 802-A, which will allow the sub-sample 102-SS to be expelled from the carrier 802-A and the swing arm 1316 allows the sample identification code to be read from the identification device 1314. In this way, the controller 1012 keeps track of the samples being tested.

In one embodiment the indexer 1312 accommodates four pairs of sub-samples 102-SS. The staging carousel 108-B accommodates thirty-six pairs of sub-samples 102-SS. In this way, the staging device 108-B accommodates sufficient sub-samples 102-SS to provide test samples to the test station 114 in the event the sub-sampler 150 is interrupted, such as by a temporary slowdown or stoppage. Likewise, the staging device 108-B has sufficient capacity to accommodate storing sub-samples 102-SS in the event testing is interrupted. The staging device 108-B acts as a buffer for other system components.

The pneumatic system 124 includes an air pump 1002 that supplies conditioned air to the sub-sampling mechanism 132-B, the sub-sample staging device 108-A, 108-B, and test station one 114. The conditioned air from the air pump 1002 is directed toward the portion of the system 100 where the sub-sample 102-SS passes. The air is conditioned to maintain a specified temperature and relative humidity to condition the sub-samples 102-SS.

The pneumatic system 124 also includes a vacuum pump 1004 connected to the sub-sample staging device 108-A, 108-B, test station one 114, and the waste device 1006. The vacuum pump 1004 is selectively connected to various pipes and equipment to pull the fibers or the sub-sample 102-SS from one location to another within the pneumatic system 124. For example, the vacuum from the vacuum pump 1004 is used to pull the fibers from the extraction drum 702-A, through the three-way valve 714-A, and to the staging device 108, where the sub-sample 102-SS is held until test station one 114 is ready to test the sub-sample 102-SS.

A controller 1012 is connected to the sub-sampling mechanism 132-B, the valve 1306, the sub-sampling staging device 108, test station one 114, and the waste device 1006. The sensor 1304 monitors the sub-sample carrier 802-B to determine if the sub-sample 102-SS is within weight limits. The controller 1012 monitors the optical sensor 1304 and controls the sub-sampling mechanism 132-B and valves 1306 to collect more fibers until the desired volume or mass of the sub-sample 102-SS is obtained. The controller 1012 monitors test station one 114 and initiates the removal of a tested sub-sample 102-SS and the transfer of the next sub-sample 102-SS to be tested from the staging device 108. For example, the controller 1012 operates various valves in the pneumatic system 124 to pull the desired sub-sample 102-SS from the staging device 108 to test station one 114.

The sub-sampling mechanism 132-B includes an extraction drum 702 with a shroud 1202 to collect the extracted fibers, a pair of jet assemblies 1204-A, 1204-B, and valves 1302-A, 1302-B supplying pressurized air to corresponding assemblies 1204-A, 1204-B.

Figure 14:
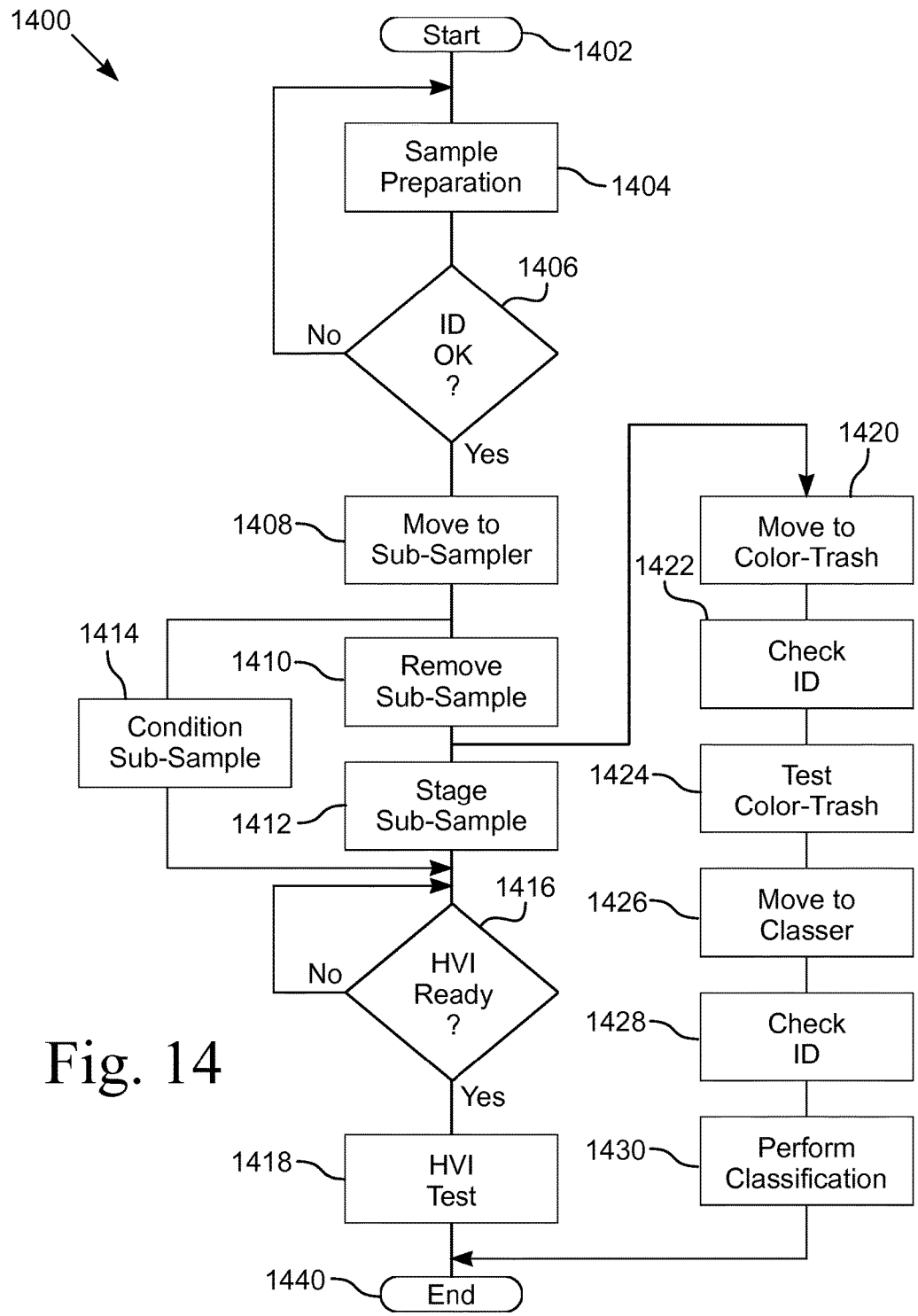
FIG. 14 is a flow diagram of one embodiment of the steps performed on a cotton sample moving through the sampling system.

FIG. 14 illustrates a flow diagram of one embodiment of the process 1400 performed on a cotton sample 102 moving through the sampling system 100-A. It is to be understood that the process 1400 is performed multiple times with the steps offset to accommodate the empty carriers 104 and the loaded primary sample carriers 104' moving through the sampling system 100-A sequentially.

At the start 1402, the step of sample preparation 1404 is performed. The loading station 120 includes a stop on the conveyor 106 for the empty primary sample carriers 104 from the classer station 118. The production assistant 140 loads a primary bale sample 102 and a bale tag 404 into a primary sample carrier 104. The next step 1406 is to check the identifying tags on the loaded primary sample carrier 104' with the scanner 128 at the loading station 120. In one embodiment, the carrier has two identical tags 402 that uniquely identify the carrier 104. The bale tag 404 uniquely identifies the bale sample 102 to be tested and is attached to the carrier 104 by the production assistant 140. In one embodiment, the carrier tags 402 and the bale tag 404 contain bar codes that are optically read by the scanner 128. If all three tags 402, 404 are readable, the loaded primary sample carrier 104' moves to the next step 1408. If not, the carrier 104' does not move and the production assistant 140 must resolve the error by performing the sample preparation step 1404 again. In another embodiment, the bale tag 404 is not secured to the loaded primary sample carrier 104', but instead is used by the production assistant 140 to associate the bale tag 404 with the carrier tags 402 on the carrier 104 containing the sample 102. In such an embodiment, the code associated with the bale tag 404 is written to a radio frequency identification (RFID) tag 402 attached to the carrier 104.

After the identification verification step 1406 is successfully performed, the next step 1408 is to move the loaded primary sample carrier 104' to the sub-sampler station 150. The next step 1410 is to remove the sub-sample 102-SS from the primary sample 102.

After removing the sub-sample 102-SS, the next step is to stage the sub-sample 102-SS for later testing at test station one 114, for example, by testing with a high volume instrument (HVI). In one embodiment, the sub-sample 102-SS is staged at the sub-sampling distribution module 108-A, where the sub-samples 102-SS are stored until they are moved to test station one 114, In another embodiment, the sub-sample 102-SS is staged at the sub-sample staging carousel 108-B until test station one 114 is ready to test the sub-sample 102-SS.

While the sub-sample 102-SS is being removed 1410 and staged 1412, the step 1414 of conditioning the sub-sample is performed. In this way, the volume of conditioning air 126 is minimized because only the sub-sample 102-SS is conditioned, not the entire primary sample 102. Additionally, the sub-sample 102-SS is stored in the staging device 108 for a time sufficient to ensure that the sub-sample 102-SS is conditioned.

After the sub-sample 102-SS is staged, the next step 1416 is to determine if the test station 1 114 is ready to test a sample. If test station one 114 is ready, the next step 1418 is to perform the test at test station one 114. In one embodiment the step 1418 of performing the test includes discarding the sub-sample 102-SS at the end of testing. In one such embodiment, the tested sub-sample 102-SS is transferred through the pneumatic system 124 to a waste device 1006.

After the step 1410 of removing the sub-sample 102-SS, the next step 1420 is to move the primary sample 102 to test station two 116. At test station two 116 the step 1022 of checking the identification tags 402, 404 is performed. After the identification is checked 1022, the step 1024 of testing is performed, for example, the color/trash test is performed. In one embodiment, the testing step 1424 is performed by the operator 146 of test station two 116 and includes performing the Cotton Micronaire test.

In another embodiment, the step 1424 of testing the color/trash is performed in conjunction with the step 1418 of the HVI test. In such an embodiment, after step 1412 of staging the sub-sample 102-SS, the loaded primary sample carrier 104' is moved to a specific color/trash station 116 associated with an HVI 114 that is available. After the step 1422 identifying the primary sample 102 identification, the associated sub-sample 102-SS is transferred to the HVI 114 for testing 1418. The color/trash station operator 146 proceeds with step 1424 by imaging the primary sample 102 while the HVI 114 performs the Cotton Micronaire test.

After the step 1424 of testing the color/trash, the step 1426 of moving the primary sample 102 to test station three 118 is performed. At test station three 118 the step 1428 of checking the identification tags 402, 404 is performed. After the identification is checked 1428, the step 1430 of performing the classification of the sample 102 is performed. In one embodiment, the classifying step 1430 is performed by the classer station operator 148 who enters the grade value and determines if the sample is being called for Specials, Studies, or Check-Lots. If called, the classer station operator 148 sets the associated primary sample 102 with the bale tag 404 aside for the other, called processes. If not called, the classer station operator 148 disposes of the primary sample 102 down a reclamation conveyor and the empty primary sample carrier 104 is returned to the loading station 120 for the next sample 102.

In one embodiment, the steps 1420, 1422, 1424 related to testing at test station two 116 are performed after the steps 1426, 1428, 1430 related to performing the classification.

After the step 1418 of performing the HVI test and the step 1430 of performing the classification are completed, the process for testing the sample 102 is ended 1440.

One embodiment of the cotton acquisition and tracking system 100 integrates an automated imaging system that eliminates the need for a separate color/trash station 116. The automated imaging system includes high resolution cameras and related analytical algorithms. In various such embodiments, the imaging system is positioned within the cotton acquisition and tracking system 100 at any of a number of different locations. Referring to FIG. 14, in one embodiment, the automated imaging system is employed prior to step 1408 of moving the sample 102 to the sub-sampler. In another embodiment, the automated imaging system is positioned at the color/trash station 116 and used as part of step 1424 of testing color/trash.

One such embodiment of the automated imaging system has the primary sample carrier 104 positioned within the imaging system, and, after the identifying tags 402, 404 have been verified, the cameras automatically move into position above and below each half of the primary sample carrier 104 to capture two images of each half of the primary sample. The captured images and calculated data are stored and then paired with the test data from the HVI that performs the classing tests (step 1430) on the representative sub-samples. Once the test data from both operations has been paired and verified for sample integrity, the primary sample carrier 104 moves to either the sub-sampler (step 1408) or to the classer (step 1426), depending upon placement of the imaging system.

Figure 15:
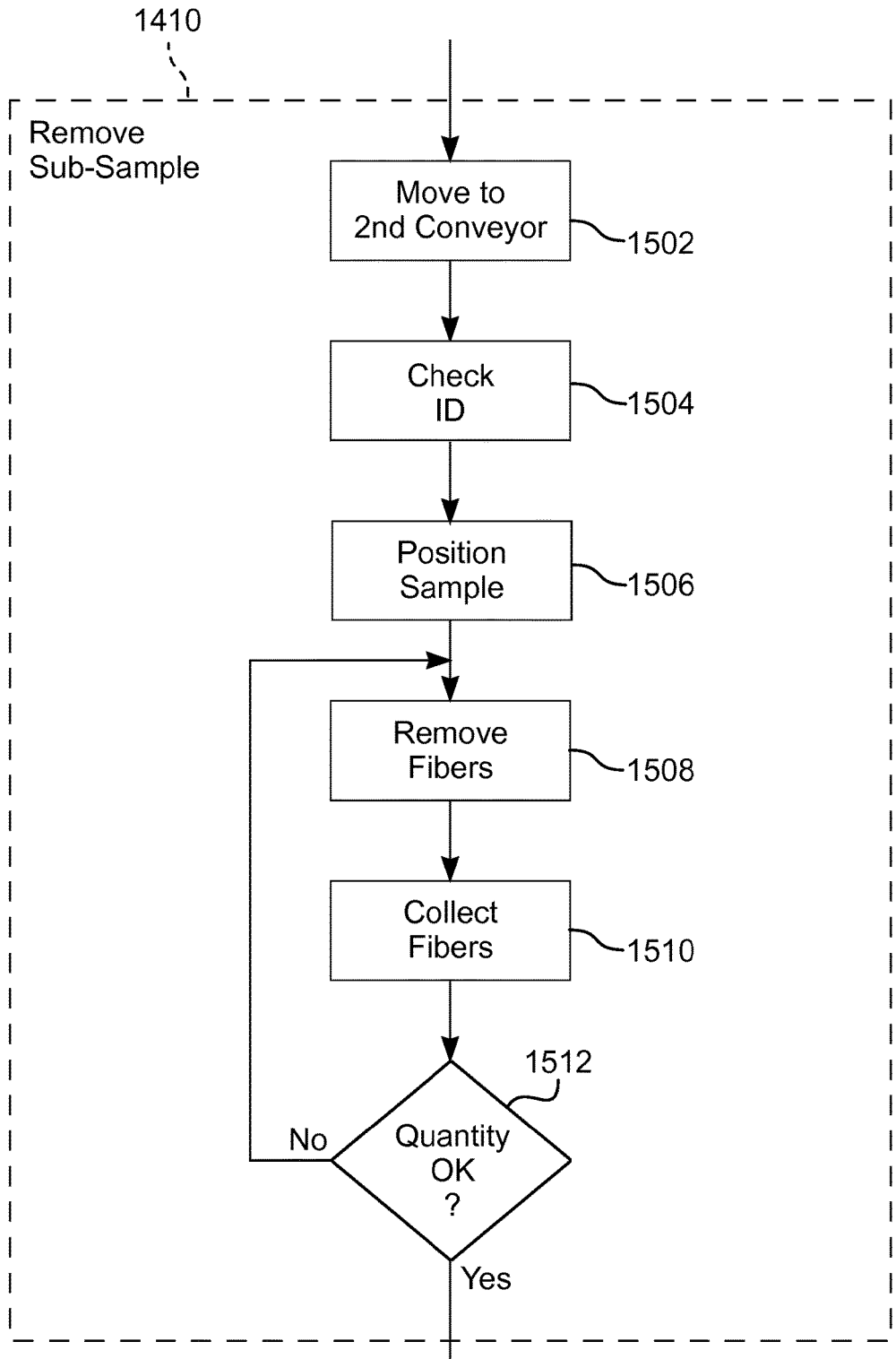
FIG. 15 is a flow diagram of one embodiment of the steps for removing the sub-sample.

FIG. 15 illustrates a flow diagram of one embodiment of the steps for removing the sub-sample 1410. At the sub-sampler station 150, the step 1410 of removing the sub-sample includes the step 1502 of moving the loaded primary sample carrier 104' from the main conveyor 106 to a second conveyor 130 and the step 1504 of checking the identity of the sample 102 in the primary sample carrier 104. The identity is checked, in one embodiment, by the scanner 128 that reads the tags 402, 404 on the sample carrier 104. Either of these two steps 1502, 1504 can be performed initially or simultaneously.

The next step 1506 is to position the sample on the second conveyor 130 such that the sub-sampling plate 204 of the primary sample carrier 104, 104' is positioned proximate the sub-sampling mechanism 132. This step 1506 includes pressing the sample 102 in the carrier 104, 104' against the sub-sampling plate or wall 204.

In one embodiment, the step 1506 of positioning the sample includes moving the filled primary sample carrier 104' to a stop adjacent the extraction drums 702. The filled primary sample carrier 104' is elevated from the conveyor 130 to align the windows 602 with the operating surface of the extraction drums 702. With the filled primary sample carrier 104' in position, a sample feed mechanism 1220 above each half of the sample 102 is lowered 1224. The sample feed mechanism 1220 includes a plurality of needles or picks 1222 that penetrate the cotton sample 102. The sample feed mechanism 1220 is operated by a pneumatic cylinder. A pressure sensor connected to the cylinder determines when the sample feed plate fully engages the sample 102 and provides a signal to stop the downward movement of the sample feed mechanism 1220. The sample feed mechanism 1220 is then moved horizontally 1226 to feed the sample 102 through the window 602 in the carrier 104-B. An optical sensor detects when the sample 602 protrudes outside the window 602 in the carrier 104-B and stops feeding the sample 102. The sample feed mechanism 1220 continues to feed the sample 102 as the extraction drum 702 extracts fibers from the sample 102.

After the positioning step 1506, the next step 1508 is to remove the fibers from the primary sample 102. In one embodiment, the fiber removing step 1508 is performed by the sub-sampling mechanism 132 picking fibers from the portion of the sample 102 protruding from the holes 214 in the sub-sampling plate 204. In another embodiment, the fiber removing step 1508 is performed by the sub-sampling mechanism 132 carding fibers from the portion of the sample 102 protruding from the holes 214 in the sub-sampling plate 204. For the embodiment where the fiber removing step 1508 is performed by carding, a extraction drum 702 moves relative to the primary sample 102.

The fibers are doffed via a vacuum from the pneumatic system 124. The next step 1510 is to collect the fibers in the sub-sample carrier 802. The pneumatic system 124 pulls the fibers from the sub-sampling mechanism 132 to the sub-sample carrier 802, where the quantity of the fibers making the sub-sample 102-SS is determined. In various embodiments, the quantity of fibers making the sub-sample 102-SS is based on weight, mass, and/or volume.

The step 1512 of determining if the quantity is correct is performed after the step of collecting fibers 1510. In one embodiment, the differential pressure across the fibers collected in the sub-sample carrier 802-A is measured by a differential pressure sensor 1008. If the differential pressure is lower than a preset limit, the measurement indicates that the collected fibers are not sufficient to meet the minimum quantity requirements. In another embodiment, the step 1512 of determining the quantity is implemented by measuring the height of the fibers in the sub-sample carrier 802-B using an optical sensor 1304.

If the collected fibers do not meet the quantity requirements as determined in step 1512, the step 1508 of removing fibers is repeated. If the collected fibers meet the quantity requirements as determined in step 1512, the step 1410 of removing the sub-sample 102-SS is completed and the process 1400 moves to the next step 1412 of staging the sub-sample 102-SS.

Figure 16:
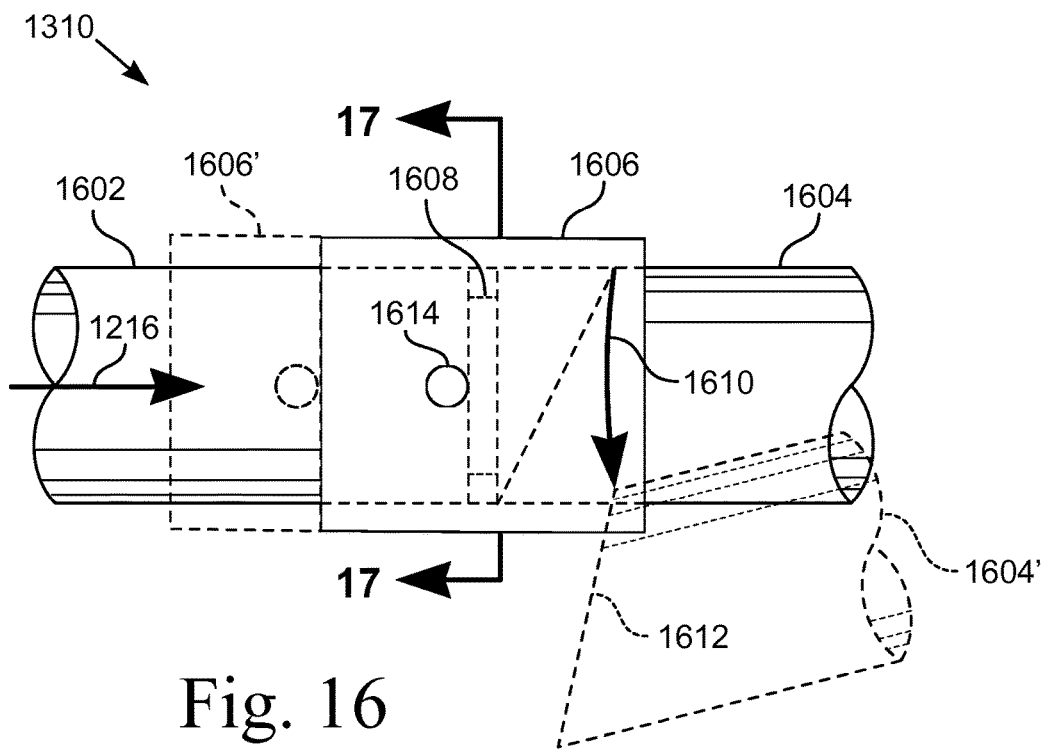
FIG. 16 is a partial side view of one embodiment of a cotton containment mechanism.
Figure 17:
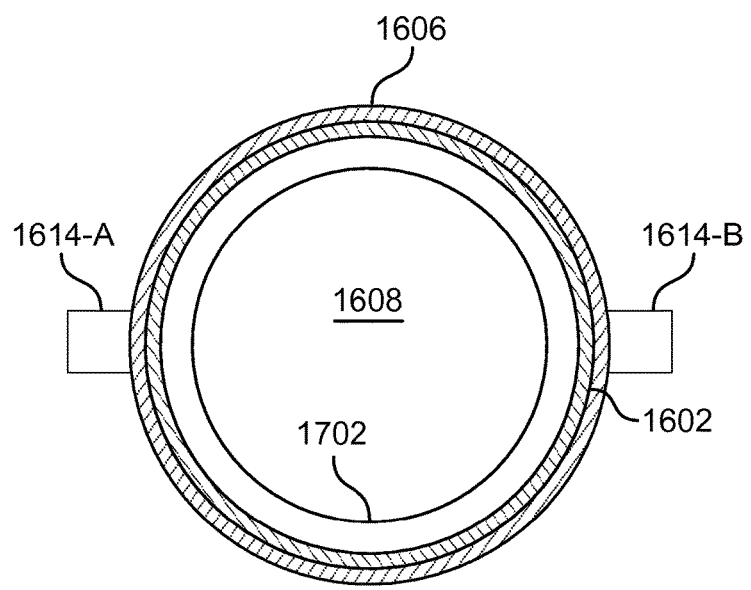
FIG. 17 is a cross-sectional view of the embodiment of the cotton containment mechanism shown in FIG. 16.

FIG. 16 illustrates a partial side view of one embodiment of a cotton containment mechanism (CCM) 1310. FIG. 17 illustrates a cross-sectional view of the embodiment of the cotton containment mechanism 1310 shown in FIG. 16. During cotton acquisition, oversized tufts, or clumps, of cotton occasionally are removed from the primary sample and enter the vacuum air stream 1216. Some clumps are so large that they cause clogs in downstream components such as diverter valves, indexer tubes, and staging tubes. Oversized clumps often adversely affect sample mass range.

The cotton containment mechanism 1310 receives extracted fibers from a flow stream 1216 moving through the inlet tube 1602. The distal end of the inlet tube 1602 has a restrictor or orifice plate 1702 with a central opening or orifice 1608. The orifice 1608 is sized to capture oversized clumps so that they do not travel further into the system. The diameter of the orifice 1608 is dependent upon the flow rate and the size of clump desired to be stopped. The outlet tube 1604 mates with the distal end of the inlet tube 1602. The two tubes 1602, 1604 have an end 1612 cut at an oblique angle such that when the outlet tube 1604 pivots downward 1610 the outlet tube 1604' clears the distal end of the inlet tube 1602. Attached to the distal end of the inlet tube 1602 and overlapping the distal end is a sleeve or collar 1606. The sleeve 1606 conforms to the outer surface of the inlet tube 1602 and ensures alignment of the inlet and outlet tubes 1602, 1604 when the tubes 1602, 1604 are in a throughflow configuration. With the outlet tube 1604' in the pivoted downward 1610 position, the cotton containment mechanism 1310 is in the clump removal configuration because the clump caught by the orifice 1608 is accessible for removal from the distal end of the inlet tube 1602. Before the cotton containment mechanism 1310 leaves the throughflow configuration, the flow 1216 through the tubes 1602, 1604 is stopped, for example, by closing the valve 1306.

In the illustrated embodiment, the collar 1606 is a cylindrical tube that slides along the inlet and outlet tubes 1602, 1604. In the throughflow configuration the collar 1606 is positioned over the joined ends 1612 of the tubes 1602, 1604. In this way, the collar 1606 ensures that the tubes 1602, 1604 are aligned and are sealed. To separate the tubes 1602, 1604, the collar 1606' is moved axially away from the joined ends 1612 such that the outlet tube 1604 is pivotable or movable 1610 such that outlet tube 1604' is out of the way and allows access to the distal end of the inlet tube 1602.

The cotton containment mechanism 1310 includes a restrictor plate 1702, optical or differential pressure sensors 1614, and separable containment chamber 1602. Restrictor plates 1702 are sized to prevent targeted mass ranges of clumps from entering the airstream downstream of the plate 1702. The sensors 1614 detect a blockage and trigger a clearing action and confirm the blockage has been cleared before the sub-sample process can be resumed. In one embodiment, the sensors 1614 include a light source 1614-A and a light sensor 1614-B. The sensors 1614 are attached to the sleeve 1606 and move with the sleeve 1606. The sensors 1614 rely upon the translucent material of the inlet tube 1602 for the optical signal from the sensors 1614 to be responsive to any buildup of fibers indicating a clump is present at the restrictor plate 1702. When a clump collects at the orifice 1608, the light from the source 1614-A is blocked by the clump and the light sensor 1614-B detects the absence of light, thereby sensing the presence of a clump needing removal. In another embodiment, the sensors 1614 are differential pressure sensors that include an upstream pressure sensor 1614-A and a downstream pressure sensor 1614-B. A differential pressure of a specified magnitude between the two sensors 1614-A, 1614-B indicates the presence of a clump. In such an embodiment, the sensors 1614 mate with an opening in the inlet tube 1602 when the sleeve 1606 is in the throughflow configuration. In another such embodiment, the differential pressure sensors 1614 tap into the inlet and outlet tubes 1602, 1604 away from the sleeve 1606, thereby avoiding having the sensors 1614 move with the sleeve 1606. The containment chamber consist of a tube 1602 with a diagonally cut distal end. The containment chamber 1602 and the outlet tube 1604 are held together with the overlapping sleeve or collar 1606.

In one embodiment, the cotton containment mechanism 1310 is a manual mechanism that detects a clump or oversized mass and allows for an operator to remove the clump or oversized mass. With the inlet tube 1602 held statically in position, the sleeve 1606 is moved axially away from the tube end 1612, thereby allowing the outlet tube 1604 to pivot in a direction 1610 away from the inlet tube 1602 and allowing the two tubes 1602, 1604 to be separated. With the two tubes 1602, 1604 separated and the cotton containment mechanism 1310 in the clump removal configuration, the clump is exposed and removed manually.

In another embodiment, the cotton containment mechanism 1310 is an automated mechanism that removes the clump or oversized mass without operator intervention. In one such embodiment, the automated cotton containment mechanism 1310 includes an actuator that slides the sleeve 1606 away from the tube end 1612 and moves the outlet tube 1604 into the clump removal configuration and a clump picker then removes the clump. In another such embodiment, the automated cotton containment mechanism 1310 includes a shuttle between the inlet and outlet tubes 1602, 1604. The orifice 1608 is in the shuttle. Upon detection of a clump in the CCM 1310, the shuttle is slide away from the tubes 1602, 1604 and a reverse air flow is used to blow the clump away from the orifice 1608 for disposal. The cleared orifice 1610 is then returned to position and the CCM 1310 is returned to the throughflow configuration.

FIG. 18 illustrates a perspective view of one embodiment of an indexer 1312 using the embodiment of the sub-sample carrier 802-B shown in FIG. 9. The indexer 1312 includes a plurality of sub-sample carriers 802-B positioned between a pair of plates 1812, 1814. The indexer 1312 rotates in a direction 1810 that positions each of the sub-sample carriers 802-B in alignment with a pair of collection inlets 1802 and a pair of extraction outlets 1806. Because the primary sample 102 is divided into halves with each half providing a sub-sample 102-SS, a pair of sub-sample carriers 802-B are associated with each primary sample 102. In the illustrated embodiment, the indexer 1312 is configured to accommodate four pairs of sub-samples 102-SS from four primary samples 102.

The top plate 1812 connects to a pair of collection inlets 1802 that has an air flow direction 1804 into a pair of receiving sub-sample carriers 802-B-R. The flow direction 1804 is such that the air stream 1804 flows into the opening in the top plate 1812, through the receiving sub-sample carrier 802-B-R, and out the opening in the bottom plate 1814. The fibers flowing in the air stream are stopped by the mesh 804 in the carrier 802-B-R. When a sub-sample 102-SS has been collected in the carrier 802-B-R, the sub-sample 102-SS is conditioned by the continuous flow of conditioned air through the carrier 802-B. After the pair of sub-samples 102-SS are collected, the indexer 1312 rotates to position a pair of empty sub-sample carriers 802-B in line with the collection inlets 1802.

The top plate 1812 connects to a pair of extraction outlets 1806 that has an air flow direction 1818 into the bottom of a pair of extraction sub-sample carriers 802-B-E. The flow direction 1818, 1808 is such that the sub-sample collected and stored in the sub-sample carrier 802-B-E is pushed out of the carrier 802-B-E by a positive air pressure applied through openings in the bottom plate 1814. The blown out sub-samples 102-SS are then routed to a staging device 108. Each carrier 802-B includes a one-way valve 906 that prevents the air flow 1818 from entering the space between the cylinders 806, 902. Instead, the positive air pressure is directed axially 1818, 1808 through the mesh 804 and carrier 802-B-E. After the sub-samples 102-SS have been extracted from the carrier 802-B-E, the indexer 1312 rotates to position another pair of sub-sample carriers 802-B in line with the extraction outlets 1806.

The illustrated embodiment of the indexer 1312 has eight sub-sample carriers 802-B. To facilitate efficiency the collection and extraction operations occur in parallel. In one such embodiment, the indexer 1312 has a pair of collection inlets 1802 and extraction outlets 1806. In this way the throughput of the indexer 1312 is increased by double. In such an embodiment, the indexer 1312 rotates 1810 in increments of two, that is, each carrier 802-B moves two slots over when the indexer 1312 is rotated.

One way to determine if the sub-sample 108-SS has sufficient mass, but not too great of a mass, is to measure the height of the fibers in each sub-sample carrier 802-B-R that is receiving fibers. For illustration purposes, FIG. 18 shows only a single optical transmitter 1824 and corresponding optical receiver 1826.

The optical transmitter 1824 emits a light beam 1828 that passes through the receiving sub-sample carrier 802-B-R. The light beam 1828 is reflected from a mirror 1822 and travels between two sub-sample carriers 802-B. The light beam 1828 is then received by the optical receiver 1826. When the height of the fibers in the receiving sub-sample carrier 802-B-R is sufficient to block the light beam 1828, the optical receiver 1826 senses the change in the light beam 1828 and communicates the status change to the controller 1012, which takes appropriate action.

The optical transmitters 1824 and receivers 1826 are set at appropriate heights. For example, four sets of sensors 1824, 1826 are positioned along the height of the two sub-sample carriers 802-B-R. The lowest sensors 1824, 1828 detect the presence of fiber in the carrier 802-B-R. Before a new sub-sample 102-SS is collected the system verifies that the previous sub-sample 102-SS has been completely removed from the carrier 802-B-R. The second higher set of sensors 1824, 1828 senses that the carrier 802-B-R has an almost complete sub-sample 102-SS. In this case the sub-sampler 150 reduces its speed of collection so that the rate of filling of the carrier 802-B-R decreases. The third set of sensors 1824, 1828 detects when the sub-sample 102-SS collection is complete. The fourth and highest set of sensors 1824, 1828 detects an overfilled condition, that is, this set detects that the carrier 802-B-R contains too much fiber. The sub-sample 102-SS is then rejected for being out of specification.

Figure 19:
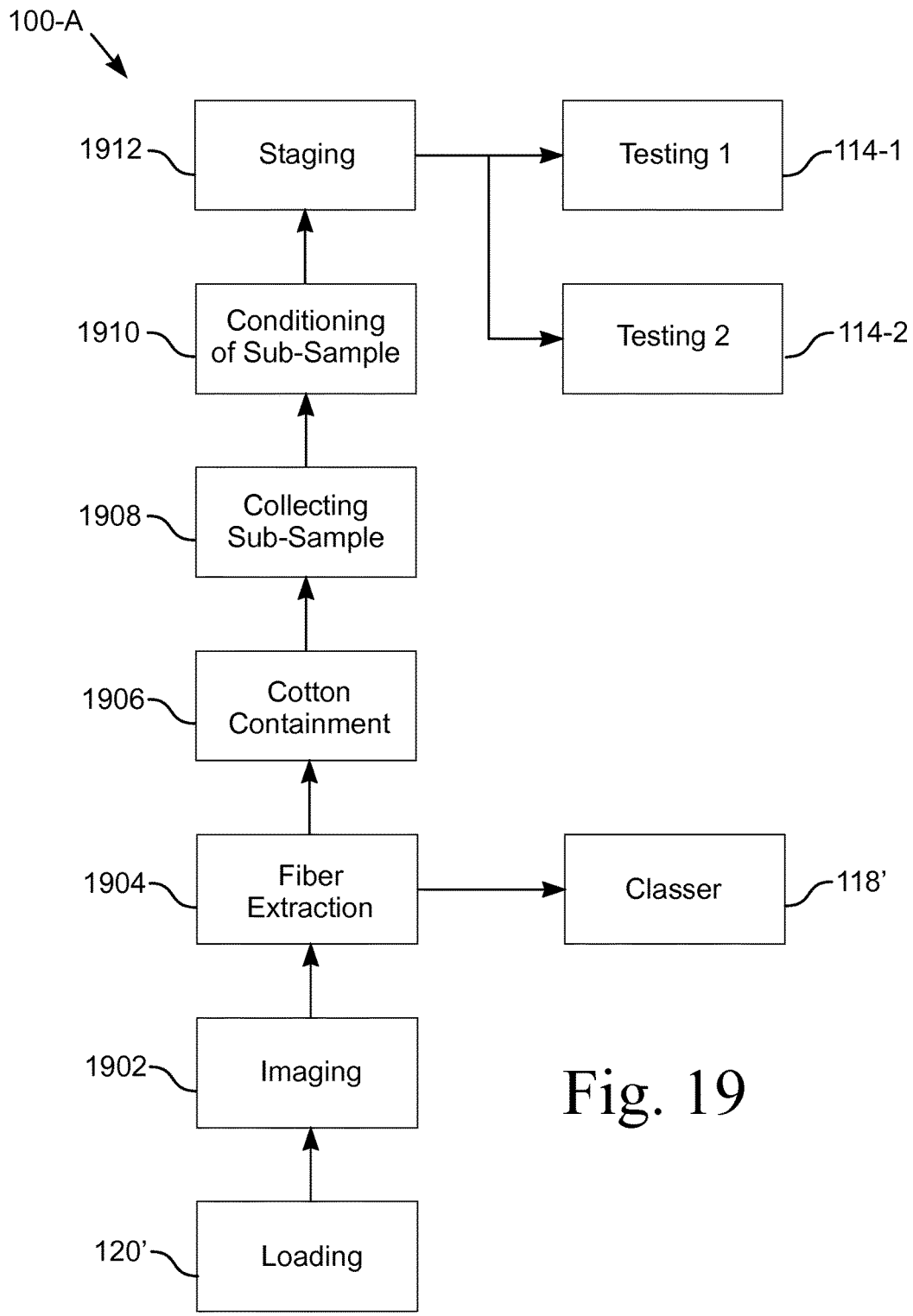
FIG. 19 is a block diagram of another embodiment of a cotton acquisition and tracking system.

FIG. 19 illustrates a block diagram showing the functions of one embodiment of a cotton acquisition and tracking system 100-A. The illustrated embodiment includes a loading station 120', such as the auto-loading station previously described. The loading station 120' transports the primary sample 102 to an imaging station 1902, such as an automated imaging system that eliminates the need for a separate color/trash station 116. The primary sample 102 is then transported to a device that performs the function of fiber extraction 1904 from the primary sample 102. The primary sample 102 is then transported to the classer station 118'. In one embodiment the classer station 118' is the final arbiter of the validity of the testing process. Generally, the classer station 118' examines the primary sample 102 after all the other testing is completed.

The fiber extraction 1904 pulls fibers from the primary sample 102. The fibers from the fiber extraction device 1904 pass through a cotton containment 1906, and then are collected 1908 into a sub-sample 102-SS before the sub-sample 102-SS is conditioned 1910. The sub-samples 102-SS are sent to the staging device 1912, where the sub-samples 102-SS are kept until the testing stations 114-1, 114-2 are ready to accept a sub-sample 102-SS. The system 100-A is configurable to accommodate multiple testing stations 114-1, 114-2, based on the throughput of the sub-sampler 150'.

In the illustrated embodiment the primary sample 102 moves from loading 120', to imaging 1902, to fiber extraction 1904, and to the classer 118', after which the primary sample 102 is discarded. In one embodiment, the primary sample 102 is minimally handled and a primary sample carrier 104 is not needed to transport the samples 102. The sub-samples 102-SS move as fibers from the device that performs the fiber extraction 1904 function to clump containment 1906 where oversized groups of fibers are restricted. The fibers are then are collected 1908 into a sub-sample 102-SS. The sub-samples 102-SS are conditioned 1910 and then move to staging 1912, where the sub-samples 102-SS are distributed to one of multiple testing stations 114-1, 114-2.

In one embodiment, the fiber extraction 1904 and clump containment 1906 functions are embodied in a sub-sampler 132 and the collecting 1908 and conditioning 1910 functions are embodied in an indexer 1312. In various embodiments, the collecting 1908 and conditioning 1910 functions are embodied in a sub-sampler 132 or a staging device 108.

Figure 20:
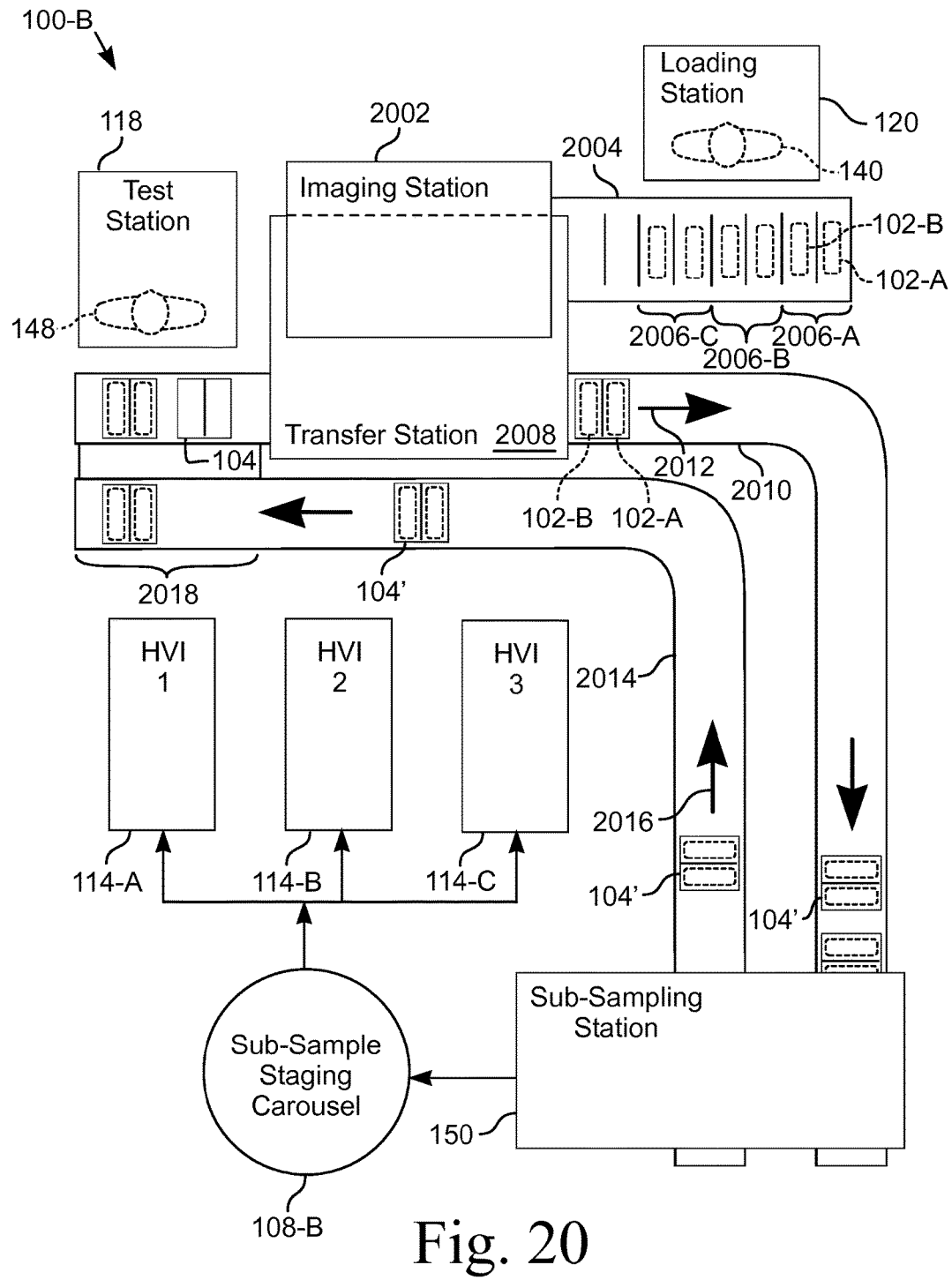
FIG. 20 is a plan view of another embodiment of a cotton acquisition and tracking system with an imaging system that is automated.

FIG. 20 illustrates a plan view of another embodiment of a cotton acquisition and tracking system 100-B with an imaging system 2002 that is automated. In the illustrated embodiment, the loading station 120 has a production assistant 140 that loads pairs of sample halves 102-A, 102-B into one of three pairs of slots 2006-A, 200-B, 2006-C formed by dividers on the conveyor 2004. Instruments sense when the samples 102 are positioned on the conveyor. The samples 102 are carried by the conveyor 2004 into the imaging station 2002, where cameras 2202 image the samples 102.

After imaging, the samples 102 enter the transfer station 2008 where the samples are transferred from the first conveyor 2004 to empty primary sample carriers 104 carried by the second conveyor 2010. The illustrated embodiment shows the imaging station 2002 and the transfer station 2008 as operating on the same part of the first conveyor 2004. In such an embodiment, the transfer of the samples 102 must occur after the samples 102 are imaged. In another embodiment the transfer station 2008 is located downstream of the imaging station 2002. In such an embodiment the transfer station 2008 operates independently of the imaging station 2002. That is, the transfer station 2008 is transferring samples 102 that have already been imaged while other samples 102 that are upstream of the transfer station 2008 are being imaged. Such a configuration has a slight improvement in efficiency with the independence of the two stations 2008, 2002, but such gains come with the price of the two stations occupying greater space.

The second conveyor 2010 moves the loaded primary sample carriers 104' in a direction 2012 toward the sub-sampling station 150 where sub-samples 102-SS are extracted and temporarily stored in the sub-sample staging carousel 108-B in a manner such as described previously.

The primary sample carriers 104 move from the second conveyor 2010 to the third conveyor 2014 in the sub-sampling station 150. The primary sample carriers 104 then move in a direction 2016 that carries them to the PSC staging area 2018 at the end of the third conveyor 2014. At the PSC staging area 2018, the primary sample carriers 104 are temporarily stored until they are moved from the third conveyor 2014 to the second conveyor 2012. The person 148 operating the test station 118 removes the sample halves 102-A, 102-B from each primary sample carrier 104 and performs a visual inspection before discarding the sample halves 102-A, 102-B. The empty primary sample carriers 104 then move into the transfer station 2008 to receive sample halves 102-A, 102-B from the transfer station 2008.

The sample halves 102-A, 102-B move in a continuous stream from the loading station 140 to the test station 118 along the conveyors 2004, 2010, 2014. The first conveyor 2004 moves in step-wise fashion as the loaded sample halves 102-A, 102-B are placed on the conveyor 2004 and positioned proximate the imaging cameras in the imaging station 2002. The second conveyor 2010 moves continuously as it moves the loaded primary sample carriers 104' from the transfer station 2008 to the sub-sampling station 150, where the loaded primary sample carriers 104' accumulate until they are loaded into the sub-sampling station 150 and transferred to the third conveyor 2014. The third conveyor 2014 moves continuously as it moves the loaded primary sample carriers 104' from the sub-sampling station 150 to the PSC staging area 2018, where the loaded primary sample carriers 104' accumulate until they are transferred to the test station 118. The sample halves 102-A, 102-B are removed from the loaded primary sample carriers 104' by the operator 148 and the empty primary sample carriers 104 move into the transfer station 2008, ready to receive new sample halves 102-A, 102-B.

The sub-samples 102-SS are removed from the sample halves 102-A, 102-B in the sub-sampling station 150. The sub-samples 102-SS are staged in the sub-sample staging carousel 108-B as they are routed to the next available test device, such as one of the high volume instruments (HVI) 114-A, 114-B, 114-C. The high volume instruments (HVI) 114-A, 114-B, 114-C perform length, strength, and/or Micronaire testing of the sub-samples 102-SS. After testing, the sub-samples 102-SS are discarded as waste. The sub-samples 102-SS move from the sub-sampling station 150, to the sub-sample staging carousel 108-B, to the high volume instrument (HVI) 114-A, 114-B, 114-C, and to the waste station via pneumatic tubes.

Figure 21:
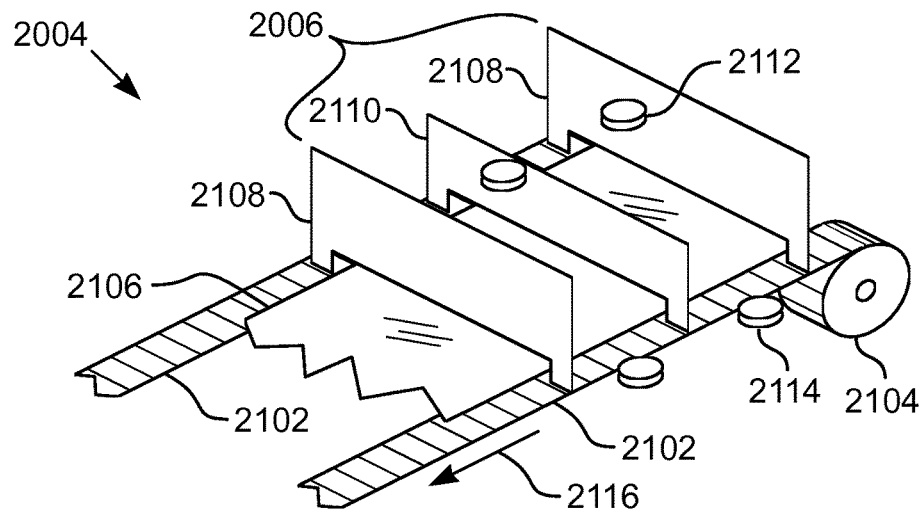
FIG. 21 is a perspective view of one embodiment of the first conveyor at the loading station.

FIG. 21 illustrates a perspective view of one embodiment of the first conveyor 2004 at the loading station 120. The first conveyor 2204 has a pair of tracks 2102 and a stationary or fixed bed 2106. The pair of tracks 2102 move on a plurality of wheels 2104 in a direction 2116 that carries the sample halves 102-A, 102-B from the loading station 120 to the imaging station 2002. Alternating tall 2108 and short 2110 uprights are attached to and move with the tracks 2102. The space between a pair of tall uprights 2108 and divided by a short upright 2110 defines a pair of slots 2006 that are configured to receive a pair of sample halves 102-A, 102-B of a single sample 102. In another embodiment each pair of slots 2006 is defined by a central divider 2110 bounded by a pair of uprights 2008 that are a different color than the central divider 2110, for example, the central divider 2110 is white and the outer uprights 2008 are black. The color difference aids the production assistant 140 in positioning the sample halves 102-A, 102-B in the correct pair of slots 2006. In such an embodiment each pair of slots 2006 do not share outer uprights 2008. Instead, the outer uprights 2008 of each pair of slots 2006-A 2006-B, 2006-C are separated by a gap that spaces a pair of sample halves 102-A, 102-B from the adjacent pair of sample halves 102-A, 102-B with a spacing that accommodates the spacing of the cameras 2202 and the pushers 2302 and boxes 2308 of the transfer station 2008.

In one embodiment, an RFID tag is positioned on the conveyor 2004 at a location corresponding to the pair of slots 2006-A, 2006-B, 2006-C. The RFID tag is written with the identifier from the bale tag for the sample.

The stationary bed 2106 is slightly elevated from the tracks 2102, which move under the stationary bed 2106. The stationary bed 2106 has a surface suitable for the sample halves 102-A, 102-B to slide along the stationary bed 2106 when the uprights 2108, 2110 push the sample halves 102-A, 102-B along the stationary bed 2106 when the conveyor 2004 is in operation. In one such embodiment, the stationary bed 2106 is polished stainless steel. The gap between the bottom of the uprights 2108, 2110 and the upper surface of the stationary bed 2106 is sufficiently small that the sample halves 102-A, 102-B will not be caught in the gap.

When the conveyor 2004 is stopped, the slots 2006 are positioned proximate the loading station 120 such that the production assistant 140 is able to place one of the sample halves 102-A, 102-B between one of the tall uprights 2108 and the short uprights 2110. A sensor 2112 determines if a sample half 102-A, 102-B is properly positioned in a slot 2006. If the sample half 102-A, 102-B is properly positioned in a slot 2006, an indicator lamp 2114 illuminates to inform the production assistant 140 that the sample half 102-A, 102-B is properly positioned. In one embodiment the indicator lamps 2114 illuminate with one of multiple colors, for example, a red color indicates that the there is no sample half 102-A, 102-B present or the sample half 102-A, 102-B is not properly positioned and a green color indicates that the sample half 102-A, 102-B is properly positioned. When all the slots 2006 have sample halves 102-A, 102-B properly in place, the conveyor moves to expose additional, empty slots 2006.

Figure 22:
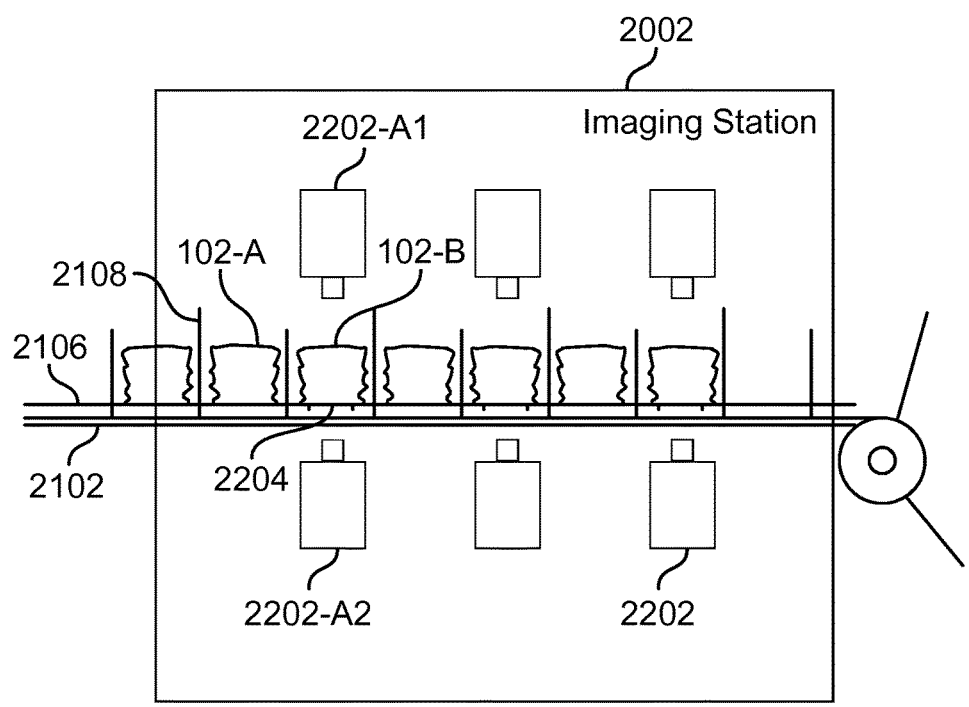
FIG. 22 is a front view of one embodiment of the imaging station showing the camera positions relative to the conveyor slots.

FIG. 22 illustrates a front view of one embodiment of the imaging station 2202 showing the positions of the cameras 2202 relative to the conveyor slots 2006. The imaging station 2002 includes a pair of cameras 2202 for each pair of slots 2006 on the first conveyor 2204. One of the pair of cameras 2202-A1 is positioned above the conveyor 2004 and the other one of the pair 2202-A2 is positioned below the conveyor 2004. The stationary bed 2106 includes windows 2204 positioned to allow the lower cameras 2202-A2 to obtain images of the bottoms of the sample halves 102-A, 102-B that are positioned above the lower camera 2202. Associated with each of the cameras 2202 is lighting of the proper intensity and temperature to allow obtaining meaningful images. In one embodiment the upper cameras 2202-A1 move toward the sample halves 102-A, 102-B before imaging and away from the sample halves 102-A, 102-B after imaging is completed.

With three pairs of slots 2006-A, 2006-B, 2006-C and three cameras 2202, the conveyor 2004 positions the first one of the sample halves 102-B proximate the cameras 2202 and then stops until the image is taken by the cameras 2202. During the time the conveyor 2204 is stopped the production assistant 148 is loading additional sample halves 102-A, 102-B on the conveyor 2004. After the first set of images is taken, the conveyor 2004 moves a half-step, which is the distance equal to one-half the width of the pair of slots 2006 such that the other one of the sample halves 102-A is positioned proximate the cameras 2202. The conveyor 2004 then stops until the image is taken by the cameras 2202. During the time the conveyor 2204 is stopped the production assistant 140 continues to load additional sample halves 102-A, 102-B on the conveyor 2004 to ensure that all the pairs of slots 2006-A, 2006-B, 2006-C are loaded with sample halves 102-A, 102-B. After the images are taken the sample halves 102-A, 102-B are transferred to primary sample carriers 104 carried by the second conveyor 2010. After the sample halves 102-A, 102-B are transferred the conveyor 2004 moves a distance equal to the three pairs of slots 2006-A, 2006-B, 2006-C, less the half-step distance.

Figure 23:
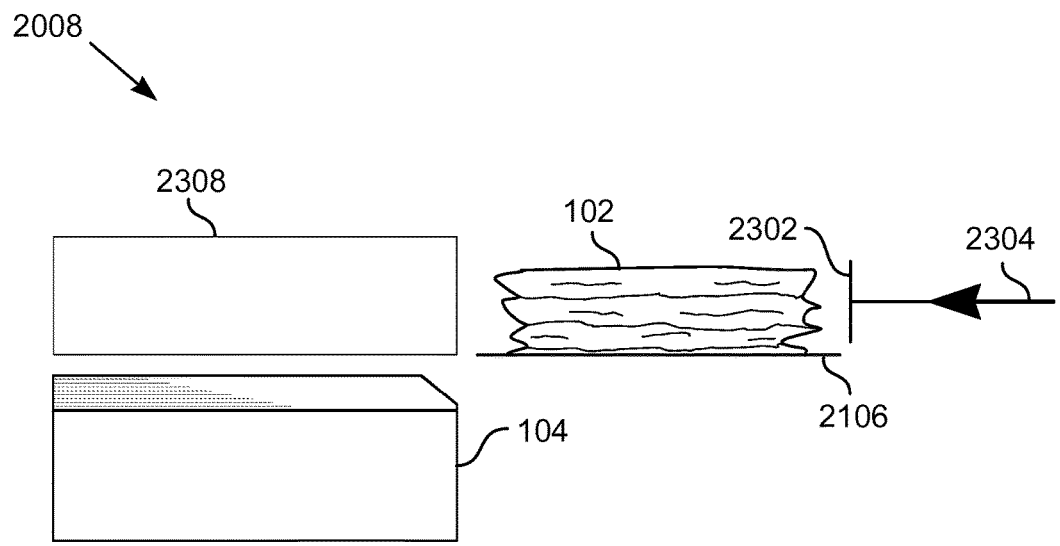
FIG. 23 is a symbolic side view of the transfer station.
Figure 24:
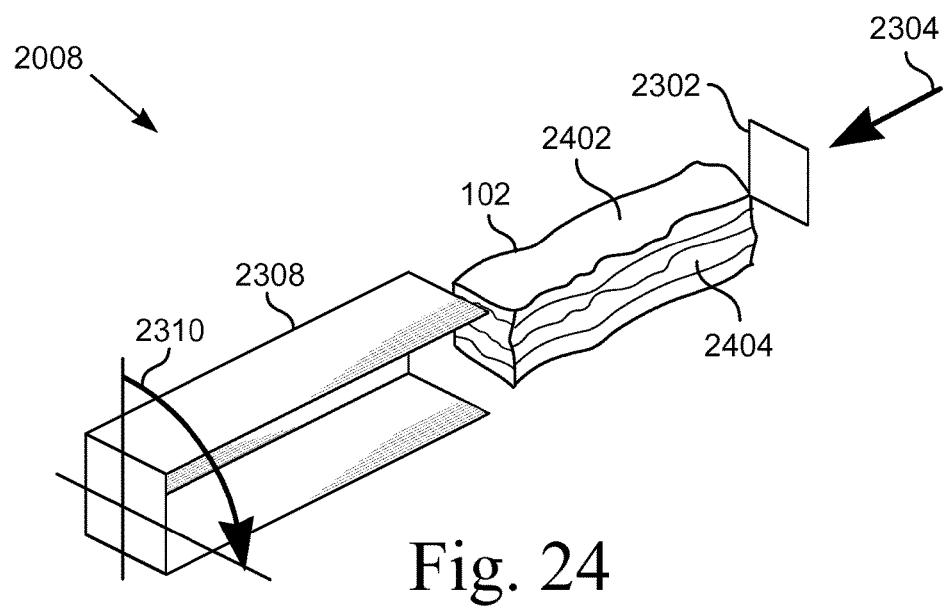
FIG. 24 is a symbolic perspective view of the transfer station.

FIG. 23 illustrates a symbolic side view of the transfer station 2008. FIG. 24 illustrates a symbolic perspective view of the transfer station 2008. The transfer station 2008 includes a pusher 2302 and a flipper box 2308 for each sample half 102-A, 102-B to be transferred. After the imaging station 2002 captures images of both pairs of the sample halves 102-A, 102-B in the three pairs of slots 2006-A, 2006-B, 2006-C, the sample halves 102-A, 102-B are transferred from the first conveyor 2004 to the second conveyor 2010. In the embodiment of the system 100-B illustrated in FIG. 20 the transfer station 2008 operates on the same sample halves 102-A, 102-B as the imaging station 2002. In such an embodiment, the pusher 2302 and the position of the camera 2202 must be coordinated to ensure that both are free to move as needed without collisions. In another embodiment the imaging station 2002 and the transfer station 2008 are at different positions on the first conveyor 2004 and operate independently.

A pusher 2302 moves linearly in a direction 2304 to force the sample 102 off the stationary bed 206 of the first conveyor 2004 and into a flipper box 2308. The flipper box 2308 rotates 2310 90 degrees to deposit the sample 102 in a primary sample carrier 104 positioned below the flipper box 2308. The primary sample carrier 104 sits on the second conveyor 2010.

The sample halves 102-A, 102-B typically consist of layers of cotton stacked upon each other. The sample halves 102-A, 102-B have a pair of opposing smooth sides 2402 and another pair of opposing sides 2404 that are rougher and corrugated. For imaging, the smooth sides 2402 provide the most representative images of the sample quality. Accordingly, the sample halves 102-A, 102-B are positioned on the first conveyor 2004 with the smooth sides 2402 on the top and bottom. For the sub-sampling mechanism 132-B, however, the corrugated sides 2404 provide a better surface for engaging the picks 1222 that move the sample halves 102-A, 102-B against the extraction drum 702. The picks 1222 more easily penetrate the sample 102 when entering through the corrugated sides 2404. The smooth sides 2402 of the sample 102 present an impediment to the picks 1222, which tend to compress the sample 102 instead of penetrating it.

In various embodiments, the pusher 2302 is moved by a hydraulic or pneumatic ram or by a linear motor. In various embodiments, the flipper box 2308 is moved by a mechanism that causes the box 2308 to pivot so that the open side rotates 90 degrees so that it is on the bottom. After the sample 102 falls or is pushed out of the flipper box 2308 and both halves of the primary sample carrier 104 are filled with the sample halves 102-A, 102-B, the primary sample carrier 104' is unlocked from its held position and permitted to move along the second conveyor 2010 to the sub-sampling station 150. In one embodiment, the RFID tag on the primary sample carrier 104' is written with the sample identifier, either using the identifier from the RFID tag on the conveyor 2004 or from the processor 2506.

Figure 25:
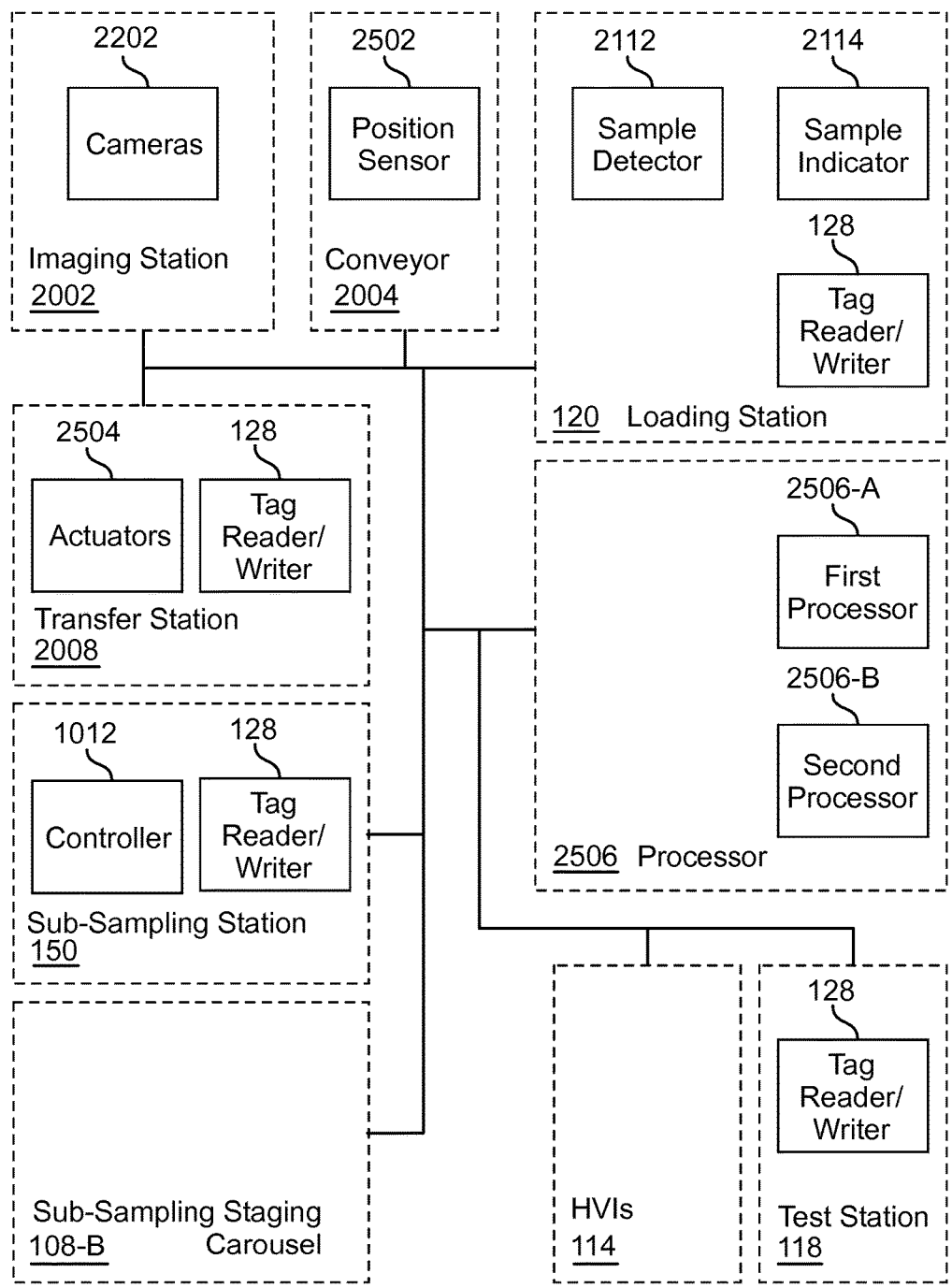
FIG. 25 is a block diagram of the embodiment of the cotton acquisition and tracking system shown in FIG. 20.

FIG. 25 illustrates a block diagram of the embodiment of the cotton acquisition and tracking system 100-B shown in FIG. 20. The various instruments and actuators are illustrated with their connections to the processor 2506. Each of the various stations includes instruments, indicators, and/or actuators that allow the system 100-B to operate with minimal operator intervention.

The loading station 120 includes sensors 2112 that detect the presence of a sample half 102-A, 102-B on the first conveyor 2004. In one embodiment, the sensors 2112 are instruments that emit and detect an optical signal reflected by the stationary bed 2106 of the first conveyor 2004. When a sample half 102-A, 102-B is in a corresponding half of a pair of slots 2006-A, 2006-B, 2006-C, the sensor 2112 detects the absence of the reflected beam, thereby sensing the presence of the sample half 102-A, 102-B. Indicators 2114 illuminate to inform the production assistant 140 of the status of each of the pairs of slots 2006-A, 2006-B, 2006-C. In order to uniquely identify the various samples 102 the bale tag 402, 404 is read by a tag reader 128 and stored in the processor 2506, along with the position of the sample half 102-A, 102-B on the conveyor as determined by the position sensor 2502 of the first conveyor 2004. In one embodiment, the position sensor 2502 is incorporated in a servomotor that drives the tracks 2102.

The imaging station 2002 includes the cameras 2202 controlled by the processor 2506. When the sample halves 102-A, 102-B are positioned proximate the cameras 2202 the processor 2506 communicates the identification of the sample 102 to the camera 2202 and initiates imaging. When imaging is complete, the camera 2202 communicates with the processor 2506, which stores the captured images along with the identification of the sample 102.

The transfer station 2008 includes actuators 2504 and a tag reader/writer 128. When a sample 102 transfers to a primary sample carrier 104, the RFID tag for that PSC 104 is written with the unique identifier.

The sub-sampling station 150 includes a controller 1012 and other associated components, such as illustrated in FIGS. 10 and 12. The sub-sampling station 150 also includes a tag reader/writer 128 for identifying the sample 102 from which the sub-samples 102-SS are taken.

The sub-samples 102-SS are staged and conditioned in the sub-sampling staging carousel 108-B. The processor 2506 communicates with the carousel 108-B in order to determine the status and control the routing of the sub-samples 102-SS.

The test devices (HVIs) 114 communicate with the processor 2506 to determine when each HVI 114-A, 114-B, 114-C is ready for the next sub-sample 102-SS and when the testing is completed for a sub-sample 102-SS. The processor 2506 sends the identification code for the sub-sample 102-SS to be tested to the HVIs 114. The HVIs 114 send the test data and the sub-sample 102-SS identification code to the processor 2506, which stores the test and identification data.

The test station 118 includes a tag reader/writer 128 to identify the sample 102 that the operator 148 is inspecting, testing, and/or classifying.

The processor 2506 is illustrated as including a first processor 2506-A and a second processor 2506-B. In one embodiment the first processor 2506-A is used for control of the system 100-B and the second processor 2506-B is used to store the data collected. The second processor 2506-B stores the test data for the samples 102 and allows all the test results for a single sample 102 to be compiled and analyzed together.

Figure 26:
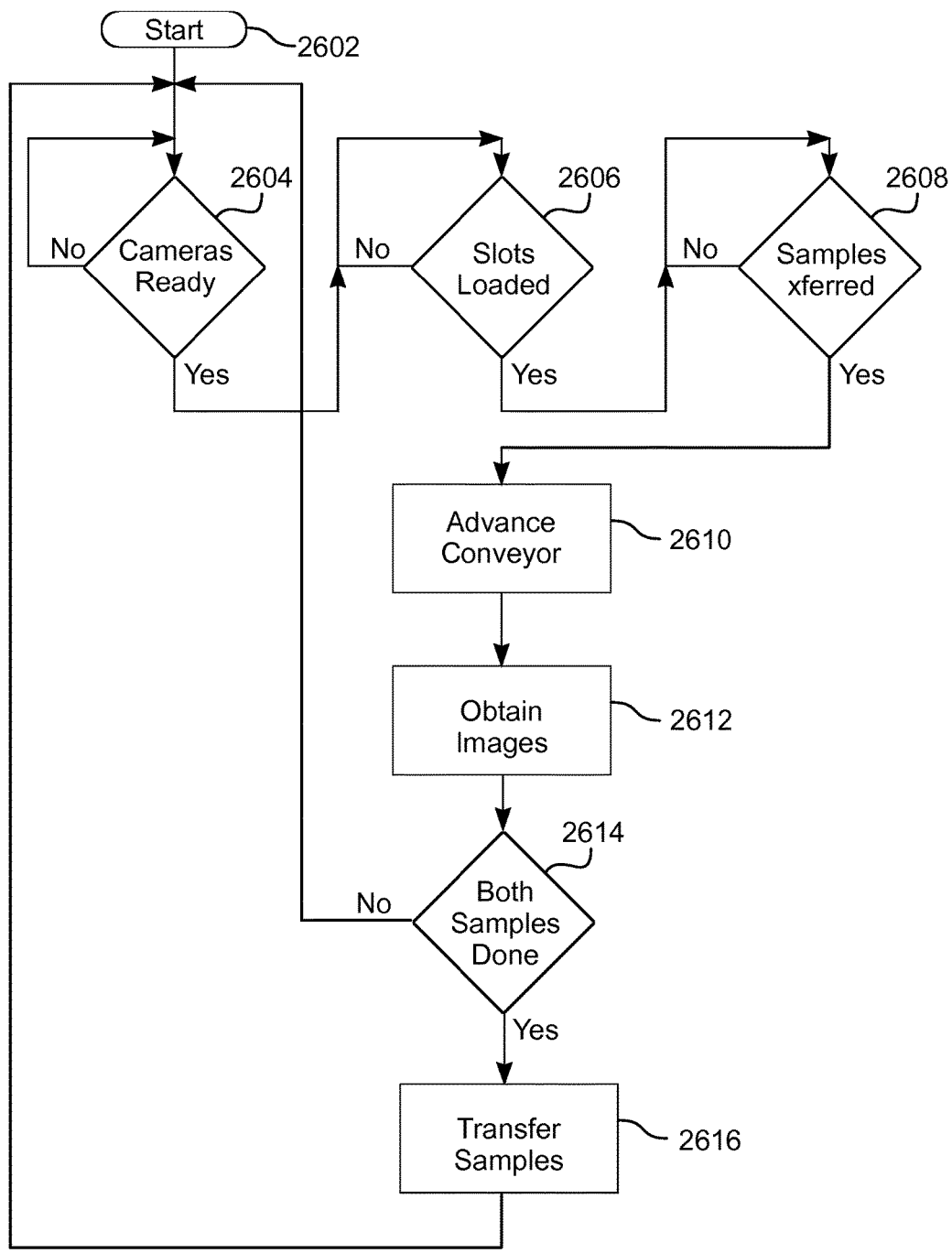
FIG. 26 is a flow diagram of the operation of one embodiment of the first conveyor shown in FIG. 20.

FIG. 26 illustrates a flow diagram of the operation of one embodiment of the first conveyor 2004 shown in FIG. 20. After the start 2602 three conditions 2604, 2606, 2608 must be satisfied before the first conveyor 2004 is moved. The order of the three conditions 2604, 2606, 2608 is variable. The first conveyor 2004 has two types of motion. One motion is a half-step, which is the distance equal to move the conveyor tracks 2102 a distance of one half of the width of the slot 2006. This distance is equal to the separation between the sample halves 102-A, 102-B so that the cameras 2202 can image each sample half 102-A, 102-B. The other conveyor motion is a batch-step that is the distance equal to the available pairs of slots 2006-A, 2006-B, 2006-C minus the half-step motion. In the illustrated embodiment there are three pairs of slots 2006-A, 2006-B, 2006-C. The conveyor 2004 moves the samples 102 in batches equal to the number of the available pairs of slots 2006-A, 2006-B, 2006-C.

One condition 2604 is to determine if the cameras 2202 are in position. In one embodiment, the cameras 2202 are moved toward the samples 102 before imaging and moved away from the samples 102 after imaging. Before the conveyor 2004 is moved the cameras 2202 must be moved away from the samples 102 so that the uprights 2108, 2110 do not strike the cameras 2202 when the conveyor 2004 moves.

Another condition 2606 is to determine if the pairs of slots 2006-A, 2006-B, 2006-C are loaded with sample halves 102-A, 102-B. The production assistant 140 scans the sample 102 and loads the sample halves 102-A, 102-B on the first conveyor 2004. In one embodiment the production assistant 140 presses a button when the available pairs of slots 2006-A, 2006-B, 2006-C are loaded. In another embodiment the sensors 2112 detect when the available pairs of slots 2006-A, 2006-B, 2006-C are loaded. After all the available pairs of slots 2006-A, 2006-B, 2006-C are loaded the condition is satisfied to move the first conveyor 2004 a distance equal to the length of the pairs of slots 2006-A, 2006-B, 2006-C.

Another condition 2608 is to determine if the sample halves 102-A, 102-B have been transferred by the transfer station 2008. This condition 2608 does not apply if the conveyor 2004 is to move a half-step. Before the conveyor 2004 moves the next batch of sample halves 102-A, 102-B into position, the sample halves 102-A, 102-B that were just imaged must be transferred by the transfer station 2008. When the transfer station 2008 completes its transfer operation, the condition 2008 is satisfied.

When all three conditions 2604, 2606, 2608 are satisfied the next step 2610 is for the first conveyor 2004 to move. If the imaging station 2002 is finished imaging half of the samples 102, the conveyor 2004 moves a half-step. If the imaging station 2002 is finished imaging all of the samples 102, the conveyor 2004 moves a batch-step. The position sensor 2502 on the conveyor 2004 provides information on the distance moved by the conveyor 2004.

After the step 2610 of moving the first conveyor 2004 is completed, the step 2612 of imaging is performed. In the illustrated embodiment there are three pairs of slots 2006-A, 2006-B, 2006-C and three pairs of cameras 2202. Each pair of cameras 2202 takes an image of one of the sample halves 102-A, 102-B in each of the pairs of slots 2006-A, 2006-B, 2006-C. The cameras 2202 take the images, which are stored in the processor 2506 and associated with the sample identification.

After a set of images is acquired, the next step 2614 is to determine if both sample halves 102-A, 102-B in each of the pairs of slots 2006-A, 2006-B, 2006-C have been imaged. If only the first one of the pair of sample halves 102-A, 102-B has been imaged, the conveyor 2004 must move a half-step to position the other one of the pair of sample halves 102-A, 102-B in position proximate the cameras 2202 for imaging. If both sample halves 102-A, 102-B have been imaged the next step 2616 is performed.

After both sample halves 102-A, 102-B have been imaged the step 2616 of transferring the samples 102 to primary sample carriers 104 on the second conveyor 2010 is performed. To transfer the sample halves 102-A, 102-B the flipper boxes 2308 are confirmed to be in position, the pushers 2302 are actuated to push the sample halves 102-A, 102-B into the flipper boxes 2308, and the pushers 2302 are returned to their initial position. At this time the pairs of slots 2006-A, 2006-B, 2006-C on the conveyor 2004 are clear and the conveyor 2004 is free to move a batch-step. To complete transfer of the sample halves 102-A, 102-B, the empty primary sample carriers 104 are confirmed to be in position under the flipper boxes 2308, the sample halves 102-A, 102-B are deposited into the primary sample carriers 104 by rotating the flipper boxes 2308 90 degrees, and the flipper boxes 2308 are returned to their initial position.

In the embodiment of the system 100-B illustrated in FIG. 20 the imaging station 2002 and the transfer station 2008 operate on the same sample halves 102-A, 102-B that occupy the sets of slots 2006-A, 2006-B, 2006-C. In such an embodiment step 2616 is performed as described above.

In another embodiment the transfer station 2008 is positioned downstream of the imaging station 2002 such that each station 2008, 2002 is operating on different sample halves 102-A, 102-B at the same time. In such an embodiment step 2616 is performed independently of step 2612 of imaging the samples 102. That is step 2616 of transferring samples 102 is performed in parallel with step 2612 of imaging the samples 102 because each of the imaging station 2002 and the transfer station 2008 is operating on different sample halves 102-A, 102-B at the same time.

Figure 27:
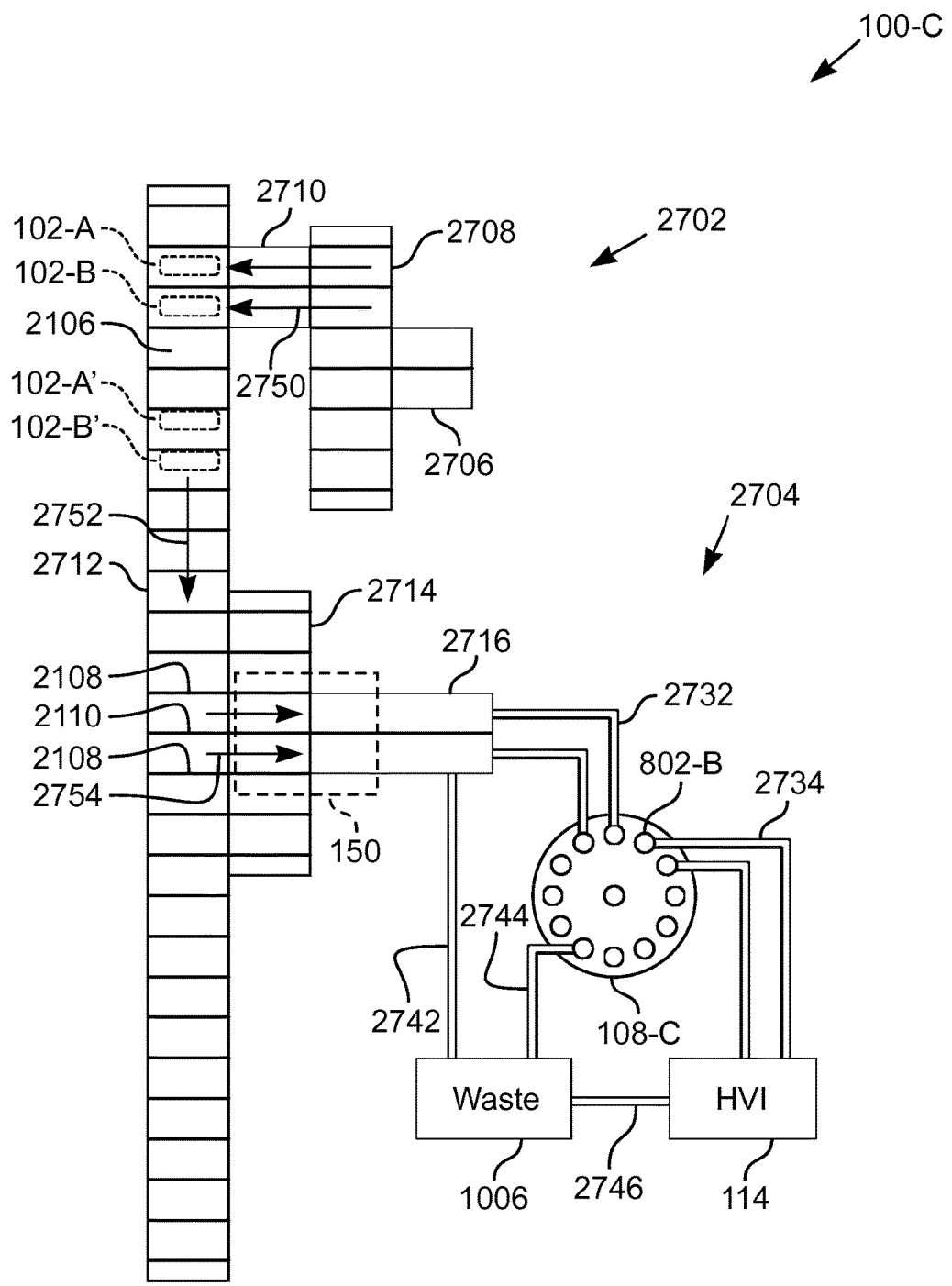
FIG. 27 is a plan view of a third embodiment of a cotton sampling system.

FIG. 27 illustrates a plan view of a third embodiment of a cotton sampling system 100-C. The sampling system 100-C includes at least one first station 2702, a main conveyor 2712, and at least one second station 2704. The length of the main conveyor 2712 is determined by the number of first and second stations 2702, 2704 desired for the system 100-C. The cotton sampling system 100-C is a modular system in that the number of stations 2702, 2704 varies to accommodate the volume of samples 102 to be tested. To minimize the length of the main conveyor, both or either of the first and second stations 2702, 2704 are positioned on both sides of the main conveyor 2712. If the length of the main conveyor 2712 accommodates the number of second stations 2704, then both first and second stations 2702, 2704 are positioned on one side of the main conveyor 2712. In this way two cotton sampling systems 100-C fit side-by-side with one system 100-C being a mirror-image of the other 100-C. The modularity of the sampling system 100-C easily accommodates various operating spaces to maximize the efficiency and utilization of the space.

The first station 2702 is where a production assistant (PA) 140 loads samples 102 onto a staging platform 2706. In one embodiment the first station 2702 is where classifying and/or imaging is performed. In other embodiments the imaging of the primary sample 102-A, 102-B is performed at a location with convenient access to the sample 102-A, 102-B, such as at the end of the main conveyor 2712 or near the HVI 114. At the first station 2702 the sample halves 102-A, 102-B move onto a first station conveyor 2708, where the sample halves 102-A, 102-B are staged before being transferred in direction 2750 to the main conveyor 2712 on the first transfer mechanism 2710.

The main conveyor 2712 is similar to the first conveyor 2004 illustrated in FIGS. 20-22. The main conveyor 2712 includes sets of uprights 2108, 2110 that push the sample halves 102-A', 102-B' (shown resting against the uprights 2108, 2110) along the stationary or fixed bed 2106 of the main conveyor 2712 in direction 2752. In one embodiment the uprights 2108, 2110 are metal sheets attached to moving tracks 2102 or other mechanism that moves the uprights 2108, 2110 along the length of the conveyor 2712.

The second station 2704 is where the sub-samples 102-SS are obtained at the sub-sampler station 150 and then transported for conditioning at the indexer 108-C and testing by the HVI 114. The sample halves 102-A, 102-B are pushed in direction 2754 from the main conveyor 2712 onto a staging conveyor 2714. The sample halves 102-A, 102-B are processed by the sub-sampler station 150, which sends the sub-samples 102-SS through the automated cotton containment mechanism (ACCM) 2716, to the indexer 108-C, and on to the HVI 114.

The sample halves 102-A, 102-B move from the main conveyor 2712 into the sub-sampler station 150. A walking beam mechanism 1220' moves each of the sample halves 102-A, 102-B against a corresponding extraction drum 702. The card pucks 722 on the drum 702 pull fibers from the sample halves 102-A, 102-B, and those fibers are blown off the drum 702 by jets 1204 and flow through an outlet 1206 to the automated cotton containment mechanism (ACCM) 2716. The ACCM 2716 blocks clumps of cotton fibers from passing through to the indexer 108-C by diverting clumps to the waste receptacle 1006 through a waste line 2742. Fibers suitable for collecting as a sub-sample 102-SS flow from the ACCM 2716 through the discharge lines 2732 into the indexer 108-C.

Once in the indexer 108-C, the fibers become collectively a sub-sample 102-SS when in a sub-sample carrier 802-B. If the sub-sample 102-SS is determined to be no good, such as by having too much mass, the indexer 108-C rotates until the sub-sample carrier 802-B is aligned with the waste tube 2744 and the sub-sample 102-SS is then sent to waste 1006 via the waste tube 2744. After the sub-sample 102-SS is conditioned the sub-sample 102-SS is transferred to the HVI 114 via transport tube 2734. After HVI testing is completed, the sub-sample 102-SS is disposed by sending it to the waste 1006 via waste tube 2746.

Figure 28:
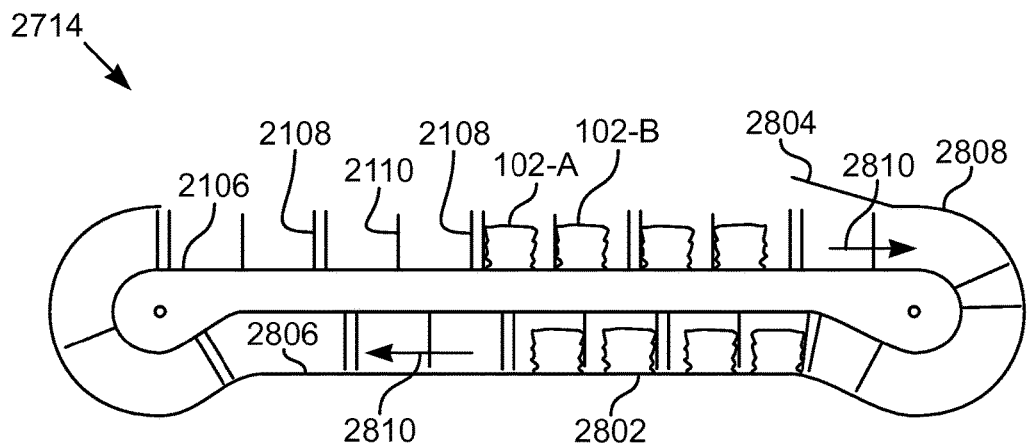
FIG. 28 is a side view of one embodiment of a conveyor with an over/under configuration.

FIG. 28 illustrates a side view of one embodiment of a conveyor 2714 with an over/under configuration. That is, the sample halves 102-A, 102-B move in a direction 2810 on the upper stationary or fixed bed 2106 and on the lower stationary or fixed bed 2806.

The staging conveyor 2714 is a short conveyor that connects the main conveyor 2712 to the sub-sampler station 150. The staging conveyor 2714 receives sample halves 102-A, 102-B from the main conveyor 2712 and stages the sample halves 102-A, 102-B until the sub-sampler station 150 obtains a valid sub-sample 102-SS for testing. For example, sample halves 102-A, 102-B in the middle of the top portion of the staging conveyor 2714 provide sub-samples 102-SS that go to the indexer 108-C for conditioning and then to the HVI 114 for testing. If the sub-sample 102-SS fails between the sub-sampler station 150 and the end of testing, then another sub-sample 102-SS must be acquired. In one configuration, the sample halves 102-A, 102-B related to a failed sub-sample 102-SS has moved to the bottom portion of the staging conveyor 2714 by the time the failed sub-sample 102-SS has been identified. The sample halves 102-A, 102-B then continue on the conveyor 2714 for another sub-sample 102-SS to be acquired. If the sub-sample 102-SS is determined to be good, then the sample halves 102-A, 102-B are removed from the conveyor 2714 to waste 1006.

The conveyor 2714 has a stationary or fixed bed 2106 on the upper portion. The ends of the conveyor 2714 and the bottom portion of the illustrated transport mechanism of the conveyor 2714 are surrounded by a shroud 2802. The shroud 2802 has three sections, namely a first shroud end 2808 where the sample halves 102-A, 102-B enter, a smooth surface or bed 2806, and a second shroud end 2808 where the sample halves 102-A, 102-B exit the lower bed 2806. The first shroud end 2808 (shown on the right side of the conveyor 2714) is where the sample halves 102-A, 102-B transition from the upper bed 2106 to the lower bed 2806. The lower bed 2806 has a smooth surface upon which the sample halves 102-A, 102-B slide when pushed by the dividers 2108, 2110, much in the same way the sample halves 102-A, 102-B slide on the stationary or fixed bed 2106. The second shroud end 2802 (shown on the left side of the conveyor 2714) is where the sample halves 102-A, 102-B transition from the lower bed 2806 to the upper bed 2106. The first shroud end 2808 of the shroud 2802 has an entry ramp 2804. The entry ramp 2804 presents a tall opening for the sample halves 102-A, 102-B in case any sample half 102-A, 102-B protrudes above a divider 2108, 2110. The first shroud end 2808 allows the sample halves 102-A, 102-B to make the transition from the stationary or fixed bed 2106 on the upper portion to the smooth surface 2806 under the conveyor 2714.

Figure 29:
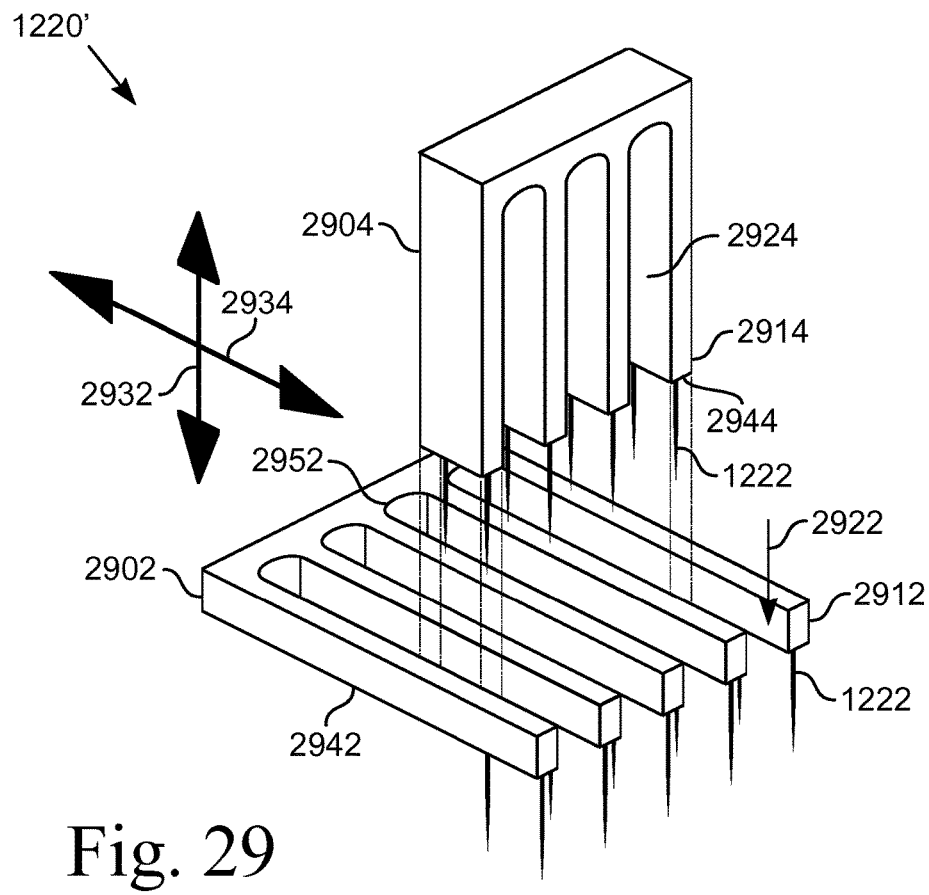
FIG. 29 is a perspective view of view of another embodiment of the sample feed mechanism for the sub-sampler station.

FIG. 29 illustrates a perspective view of another embodiment of the sample feed mechanism 1220' for the sub-sampler station 150. The sample feed mechanism 1220' is a walking beam configuration where the two pressure hands 2902, 2904 move in concert to advance the sample half 102-A, 102-B against the drum 702. The sample feed mechanism 1220' illustrated in FIG. 29 is best understood by reference to the first embodiment of the sample feed mechanism 1220 illustrated in FIG. 12.

Both the horizontal pressure hand 2902 and the vertical pressure hand 2904 reciprocate in a vertical direction 2932 and a horizontal direction 2934. The horizontal pressure hand 2902 includes multiple fingers or tines 2912 that extend longitudinally in the direction 2934 that the sample half 102-A, 102-B is to move. The vertical pressure hand 2904 includes multiple fingers or tines 2914 that extend perpendicular to the tines 2912 of the horizontal pressure hand 2902. Between each pair of the tines 2912 of the horizontal pressure hand 2902 is a space 2922 into which the tines 2914 of the vertical pressure hand 2904 fit. Likewise, between each pair of the tines 2914 of the vertical pressure hand 2904 is a space 2924 into which the tines 2912 of the horizontal pressure hand 2902 fit.

Extending from the bottom surface 2942 of the horizontal pressure hand 2902 is a plurality of spaced apart picks 1222. Extending from the bottom surface 2944 of the vertical pressure hand 2904 is a plurality of spaced apart picks 1222. The picks 1222 penetrate the sample half 102-A, 102-B with the bottom surfaces 2942, 2944 contacting the top surface of the sample half 102-A, 102-B. In this way the sample half 102-A, 102-B is securely held in place relative to the pressure hands 2902, 2904 when the hands 2902, 2904 advance the sample half 102-A, 102-B toward the drum 702.

In operation the pressure hands 2902, 2904 walk the sample half 102-A, 102-B toward the drum 702. Initially, the horizontal pressure hand 2902 is positioned away from the drum 702 when the hand 2902 moves in the downward direction 2932 so that the picks 1222 engage the sample half 102-A, 102-B. At the same time the vertical pressure hand 2904 is positioned away from the drum 702 when the hand 2904 moves in the downward direction 2932 so that the picks 1222 engage the sample half 102-A, 102-B. The tines 2914 of the vertical pressure hand 2904 are proximate the inside end 2952 of the horizontal pressure hand 2902. The two pressure hands 2902, 2904 then move together toward the drum 702, thereby forcing the sample half 102-A, 102-B against the drum 702.

When the horizontal pressure hand 2902 reaches its limit of travel toward the drum 702 the horizontal pressure hand 2902 moves in the upward direction 2932 away from the sample half 102-A, 102-B until the picks 1222 disengage the sample half 102-A, 102-B. The horizontal pressure hand 2902 then moves away from the drum 702 back to its initial position. When the hand 2902 returns to its initial position, the hand 2902 moves in the downward direction 2932 such that the picks 1222 engage the sample half 102-A, 102-B. While the horizontal pressure hand 2902 is moving back to its initial position the vertical pressure hand 2904 continues forcing the sample half 102-A, 102-B toward the drum 702. In this way the sample half 102-A, 102-B is continuously fed against the drum 702 while the horizontal pressure hand 2902 walks back to its initial position.

In a similar manner when the vertical pressure hand 2904 reaches its limit of travel toward the drum 702 the vertical pressure hand 2904 moves in the upward direction 2932 away from the sample half 102-A, 102-B until the picks 1222 disengage the sample half 102-A, 102-B. The vertical pressure hand 2904 then moves away from the drum 702 back to its initial position. When the hand 2904 returns to its initial position, the hand 2904 moves in the downward direction 2932 such that the picks 1222 engage the sample half 102-A, 102-B. While the vertical pressure hand 2904 is moving back to its initial position the horizontal pressure hand 2902 continues forcing the sample half 102-A, 102-B toward the drum 702. In this way the sample half 102-A, 102-B is continuously fed against the drum 702 while the vertical pressure hand 2904 walks back to its initial position.

Figure 30:
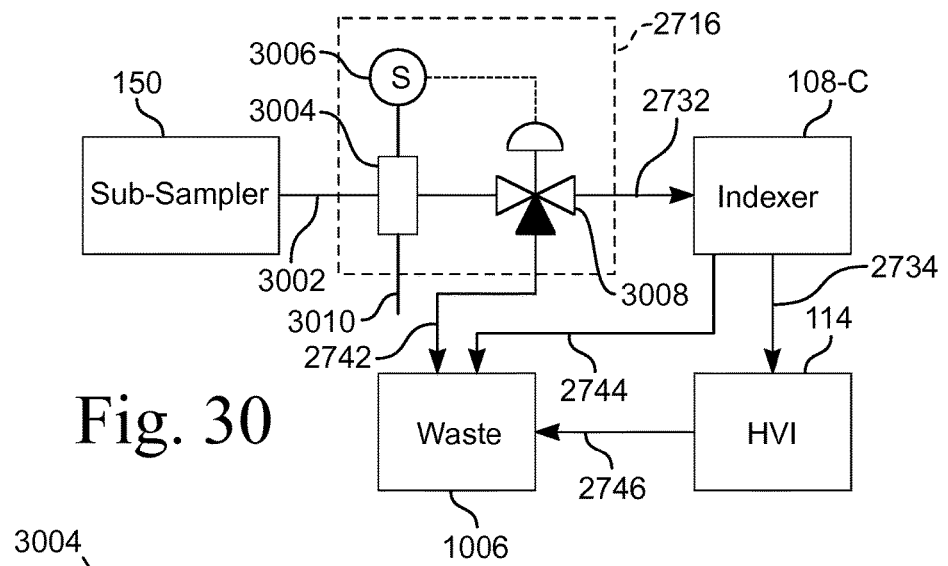
FIG. 30 is a simplified piping and instrumentation diagram of another embodiment of a cotton sampling system shown in FIG. 27.

FIG. 30 illustrates a simplified piping and instrumentation diagram of the embodiment of the cotton sampling system 100-C shown in FIG. 27. The sub-sampler station 150 receives sample halves 102-A, 102-B and outputs fibers for the sub-samples 102-SS through a vacuum line 3002. The fibers pass through an automated cotton containment mechanism (ACCM) 2716 to an indexer 108-C through a vacuum line 2732. The fibers are collected into sub-samples 102-SS at the indexer 108-C, where the sub-samples 102-SS are conditioned. The conditioned sub-samples 102-SS are transported to the HVI 114 through another vacuum line 2734. Vacuum lines 2742, 2744, 2746 transport sub-samples 102-SS to the waste receptacle 1006 from the ACCM 2716, the indexer 108-C, and the HVI 114, respectively.

Figure 31:
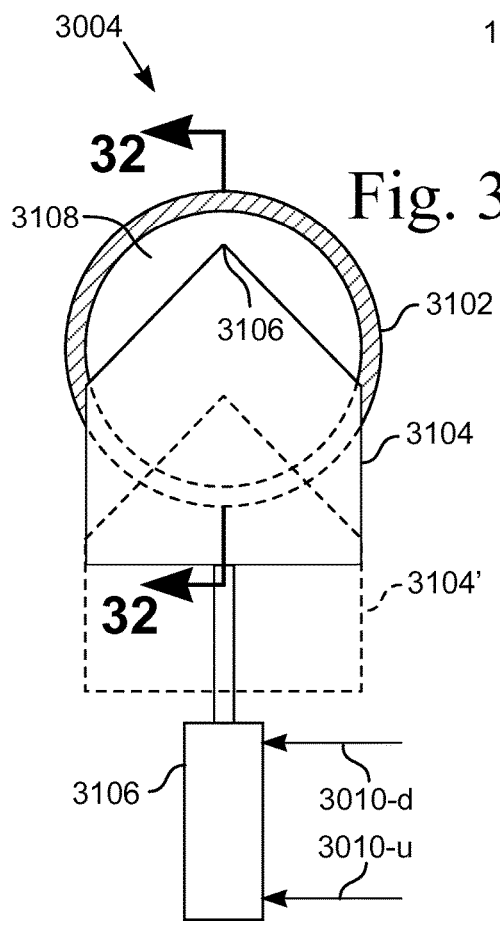
FIG. 31 is a cross-sectional view into a gate valve for one embodiment of an automated cotton containment mechanism (ACCM).
Figure 32:
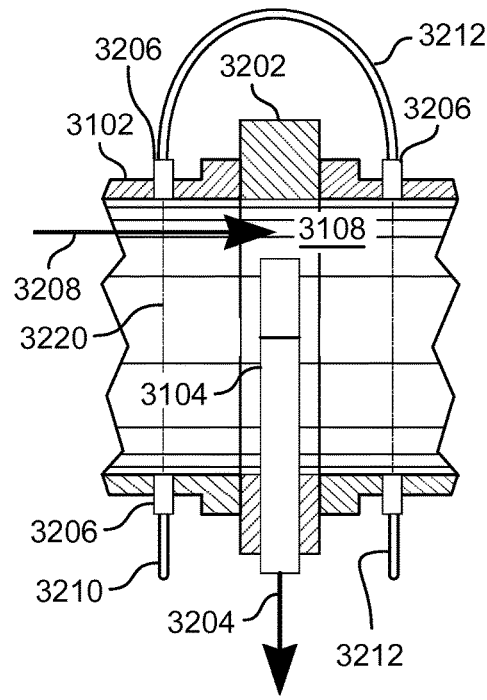
FIG. 32 is a cross-sectional view of the gate valve shown in FIG. 28.

The automated cotton containment mechanism (ACCM) 2716 illustrated in FIGS. 30-32 is best understood by reference to the embodiment of the cotton containment mechanism 1310 illustrated in FIGS. 13, 16, & 17. The ACCM 2716 includes a gate valve 3004 with a clump sensor 3006 operatively connected to a 3-way diverter valve 3008.

When a clump is detected by the clump sensor 3006, the sub-sampler 150 stops and the diverter valve 3008 operates to divert air flow from the ACCM 2716 to the waste receptacle 1006. In one embodiment, the indexer 108-C dumps the sub-sample 102-SS being collected and the sub-sample collection process begins anew. The diverter valve 3008 returns to its normal position after clearing the clump from the system and the sub-sampler 150 continues. The normal position of the diverter valve 3008 is with flow from the ACCM 3004 going to the indexer 108-C. The automated cotton containment mechanism (ACCM) 2716 is an automated mechanism that removes the clump or oversized mass without operator intervention.

FIG. 31 illustrates a cross-sectional view into a gate valve for one embodiment of an automated cotton containment mechanism (ACCM). FIG. 32 illustrates a cross-sectional view of the gate valve shown in FIG. 31. The gate valve 3004 includes a gate 3104 that moves inside a housing 3202. The gate 3104 moves in a vertical direction 3204 between a normal position 3104 and a dump position 3104'. In the normal position the gate 3104 defines a restricted opening 3108 in the pipe 3102 that is sufficient for the fibers to pass 3208. The gate 3104 has a distal end 3106 that forms a point that is about 90 degrees. When a clump forms or otherwise encounters the gate 3104, the clump sensor 3006 detects the clump.

In the illustrated embodiment the clump sensor 3006 includes an optical source 3210 connected to an optical coupling 3206 in the pipe 3102, and the optical coupling transmits a light beam 3220 into the pipe 3102. The light beam 3220 passes through the pipe 3102 to an opposite optical coupling 3206 that communicates with an optical pipe that terminates in another optical coupling 3206 on the other side of the gate 3104. The light beam 3220 continues through the pipe 3102 to another optical coupling 3206 that is attached to a light pipe or optical fiber 3212 that is coupled to an optical sensor or detector. The optical sensor provides a signal that operates the diverter valve 3008, either directly or through the controller 1012. The light path 3220 through the pipe 3102 is such that any clump stopped by the gate 3104 will break the light beam 3220 either on the upstream side of the gate 3104 or on the downstream side when a portion of the clump extends through the opening 3108.

The gate 3104 is operated by a pneumatic cylinder 3106 with an air supply 3010 providing motive force. When the light beam 3220 is broken by a clump, air is supplied through one line 3010-*d* to force the gate 3104 in the dump position 3104' where the clump passes through the valve 3008. When the light beam 3220 is reestablished the air line 3010-*u* provides air to the cylinder 3106 to move the gate 3104 to the normal position.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for acquiring, conditioning, and testing cotton sub-samples, said apparatus comprising:
   a first conveyor with a plurality of pairs of slots configured to move along a length of said first conveyor, each one of said pair of slots configured to receive a pair of sample halves, said first conveyor having a stationary bed;
   a loading station positioned adjacent said first conveyor, said loading station configured to position each one of said pair of sample halves in a corresponding one of said pairs of slots on said first conveyor, said loading station including a reader responsive to an identification of said pair of sample halves;
   an imaging station positioned proximate said conveyor downstream of said loading station, said imaging station including a first camera positioned above said stationary bed of said first conveyor, said imaging station including a second camera positioned under a window in said stationary bed of said first conveyor; and
   a transfer station on said first conveyor, said transfer station configured to transfer said pair of sample halves from said first conveyor to a sub-sampler.

2. The apparatus of claim 1 wherein each one of said plurality of pairs of slots associated with said loading station has an associated sensor that detects the presence of a corresponding one of said pair of sample halves.

3. The apparatus of claim 1 wherein each one of said plurality of pairs of slots has an associated RFID tag that stores an identification code corresponding to said identification of said pair of sample halves received by said one of said plurality of pairs of slots.

4. The apparatus of claim 1 wherein said sub-sampler includes a sample feed mechanism and a cotton fiber extraction mechanism, said sample feed mechanism configured to feed one of said pair of sample halves into said cotton fiber extraction mechanism for extracting a sub-sample of a plurality of fibers from said one of said pair of sample halves.

5. The apparatus of claim 1 further including a device for capturing a clump traveling downstream through a pneumatic routing system from said sub-sampler, a detector responsive to said clump in said device, and a valve operatively connected to said detector, said clump defined as a tangled mass of a plurality of fibers, said valve having a first position where said plurality of fibers flows from said device to a first downstream position, said valve having a second position where said plurality of fibers flows from said device to a second downstream position, wherein upon said detector determining said clump is captured by said device, said detector causes said valve to move into said second position and said detector causes said device to release said clump.

6. The apparatus of claim 1 further including an indexer that includes a plurality of sub-sample carriers, at least one of said plurality of sub-sample carriers being a receiving carrier configured to receive a plurality of fibers from said sub-sampler through a pneumatic routing system, said receiving carrier having a sensor that detects when a valid sub-sample is received by said receiving carrier.

7. The apparatus of claim 6 wherein said indexer further includes a mechanism for applying conditioned air to said sub-sample after said sub-sample is collected in said receiving carrier.

8. An apparatus for automating handling and image acquisition of cotton samples, said apparatus comprising:
   a first conveyor having a transport mechanism and a stationary bed, said first conveyor including a plurality of slots connected to said transport mechanism;
   a loading station positioned adjacent said first conveyor, each one of said plurality of slots configured to receive a sample of cotton at said loading station;
   an imaging station positioned proximate said conveyor downstream of said loading station, said imaging station capturing a first image of a first side of said sample when said sample is positioned at said imaging station by said first conveyor, said imaging station capturing a second image of a second side of said sample; and
   a transfer station on said first conveyor, said transfer station configured to transfer said sample from said first conveyor off said first conveyor;
   whereby said first conveyor receives said sample at said loading station, said first conveyor transports said sample from said loading station to said imaging station, and said transfer station offloads said sample from said conveyor after said imaging station obtains said first and second images.

9. The apparatus of claim 8 wherein said plurality of slots are grouped into a plurality of pairs of slots, each one of said plurality of pairs of slots is defined by a central divider and an outer divider, said central divider separating a first sample from a second sample, said first sample and said second sample defining a primary sample of cotton, and said outer divider separating said first sample in a first pair of slots from said second sample in a second pair of slots.

10. The apparatus of claim 9 wherein each one of said plurality of pairs of slots has an associated RFID tag with an identification code corresponding to an identifier associated with said first sample and said second sample in said each one of said plurality of pairs of slots.

11. The apparatus of claim 8 wherein one of said plurality of slots associated with said loading station has a sensor responsive to the presence of said sample in said one of said plurality of slots.

12. The apparatus of claim 8 wherein said imaging station includes a first camera positioned above said stationary bed of said first conveyor, and said imaging station includes a second camera positioned under a window in said stationary bed of said first conveyor.

13. The apparatus of claim 8 wherein said transfer station includes a pusher configured to engage said sample in one of said plurality of slots, and said pusher configured to move said sample out of said one of said plurality of slots and off of said first conveyor.

\* \* \* \* \*